US009652955B1

(12) United States Patent
Ray et al.

(10) Patent No.: US 9,652,955 B1
(45) Date of Patent: May 16, 2017

(54) REAL-TIME ASSET LOCATION SYSTEM AND METHOD WITH LONG-RANGE WIRELESS BACKHAUL

(71) Applicant: Link Labs, Inc., Annapolis, MD (US)

(72) Inventors: Brian Emery Ray, Annapolis, MD (US); Mark Olden Bloechl, Elkridge, MD (US)

(73) Assignee: Link Labs, INC., Annapolis, MD (US)

( * ) Notice: Subject to any disclaimer, the term of this patent is extended or adjusted under 35 U.S.C. 154(b) by 0 days.

(21) Appl. No.: 15/187,844

(22) Filed: Jun. 21, 2016

(51) Int. Cl.
G08B 13/14 (2006.01)
G08B 23/00 (2006.01)
G08B 17/06 (2006.01)
A61F 13/15 (2006.01)
G06Q 10/08 (2012.01)
G07B 15/06 (2011.01)
G08B 13/24 (2006.01)
G01S 5/02 (2010.01)

(52) U.S. Cl.
CPC ........ *G08B 13/2462* (2013.01); *G01S 5/0294* (2013.01)

(58) Field of Classification Search
CPC .......... G08B 13/14; G08B 23/00; G08B 1/08; A61F 13/15
USPC ......... 340/572.1, 539.13, 539.21, 10.1, 10.5; 604/361
See application file for complete search history.

(56) References Cited

U.S. PATENT DOCUMENTS

| 5,920,287 | A  | * | 7/1999  | Belcher   | G01S 5/021   |
|           |    |   |         |           | 342/450      |
| 6,469,628 | B1 | * | 10/2002 | Richards  | G01S 13/42   |
|           |    |   |         |           | 340/539.1    |
| 7,141,715 | B2 | * | 11/2006 | Shapira   | A61F 13/42   |
|           |    |   |         |           | 340/573.6    |
| 7,242,294 | B2 | * | 7/2007  | Warrior   | H04B 7/18506 |
|           |    |   |         |           | 340/539.11   |
| 7,411,921 | B2 | * | 8/2008  | Strong    | G01S 5/02    |
|           |    |   |         |           | 340/10.1     |
| 7,518,500 | B2 | * | 4/2009  | Aninye    | G07C 9/00111 |
|           |    |   |         |           | 340/506      |
| 7,973,655 | B2 | * | 7/2011  | Blinnikka | G08B 13/1427 |
|           |    |   |         |           | 340/539.13   |

(Continued)

Primary Examiner — Nam V Nguyen
(74) Attorney, Agent, or Firm — Charles B. Lobsenz; Brian Buck; Potomac Law Group, PLLC

(57) ABSTRACT

A system and method for transmitting information using first and second wireless communication protocols, including an object having a short range radio frequency signal transmitter for transmitting a signal using the first protocol, the signal including information transmitted from the object; a collector including a signal receiver for receiving the signal transmitted by the short range radio frequency transmitter and further including a collector transmitter that transmits a collector signal using the second protocol via a low power wide area network, the collector signal including the information transmitted from the object; a gateway in wireless communication with the collector via the low power wide area network, the gateway including a gateway receiver for receiving the collector signal; a processing application for processing the information transmitted from the object and creating an information processing outcome; and an end user terminal having an interface for displaying the information processing outcome.

29 Claims, 18 Drawing Sheets

(56) References Cited

U.S. PATENT DOCUMENTS

| | | | |
|---|---|---|---|
| 8,026,814 B1* | 9/2011 | Heinze | G06Q 10/06 340/10.1 |
| 8,368,555 B2* | 2/2013 | Gilbert | G01D 4/008 307/29 |
| 8,831,627 B2* | 9/2014 | Aninye | B60R 25/1004 340/539.11 |
| 8,849,926 B2* | 9/2014 | Marzencki | H04L 61/6081 709/206 |
| 9,328,857 B2* | 5/2016 | Conte | F16L 55/1652 |
| 9,439,041 B2* | 9/2016 | Parvizi | H04W 4/025 |
| 2005/0113132 A1* | 5/2005 | Irsheid | H03F 1/3247 455/552.1 |
| 2005/0250519 A1* | 11/2005 | Samuel | G01C 21/20 455/457 |
| 2007/0001813 A1 | 1/2007 | Maguire et al. | |
| 2007/0004426 A1* | 1/2007 | Pfleging | H04W 8/14 455/456.1 |
| 2007/0046459 A1 | 3/2007 | Silverman et al. | |
| 2010/0131567 A1 | 5/2010 | Dorogusker et al. | |
| 2012/0311149 A1 | 12/2012 | Trevino et al. | |
| 2013/0060351 A1* | 3/2013 | Imming | G06Q 10/08 700/13 |
| 2013/0065603 A1 | 3/2013 | Hovav | |
| 2013/0314210 A1 | 11/2013 | Schoner et al. | |
| 2013/0317944 A1 | 11/2013 | Huang et al. | |
| 2014/0149004 A1 | 5/2014 | Best et al. | |
| 2015/0282113 A1 | 10/2015 | Costa | |
| 2015/0296332 A1 | 10/2015 | Lee et al. | |
| 2015/0356498 A1* | 12/2015 | Casanova | G07B 15/063 705/13 |
| 2016/0012196 A1 | 1/2016 | Mark et al. | |
| 2016/0105762 A1 | 4/2016 | Singh et al. | |

* cited by examiner

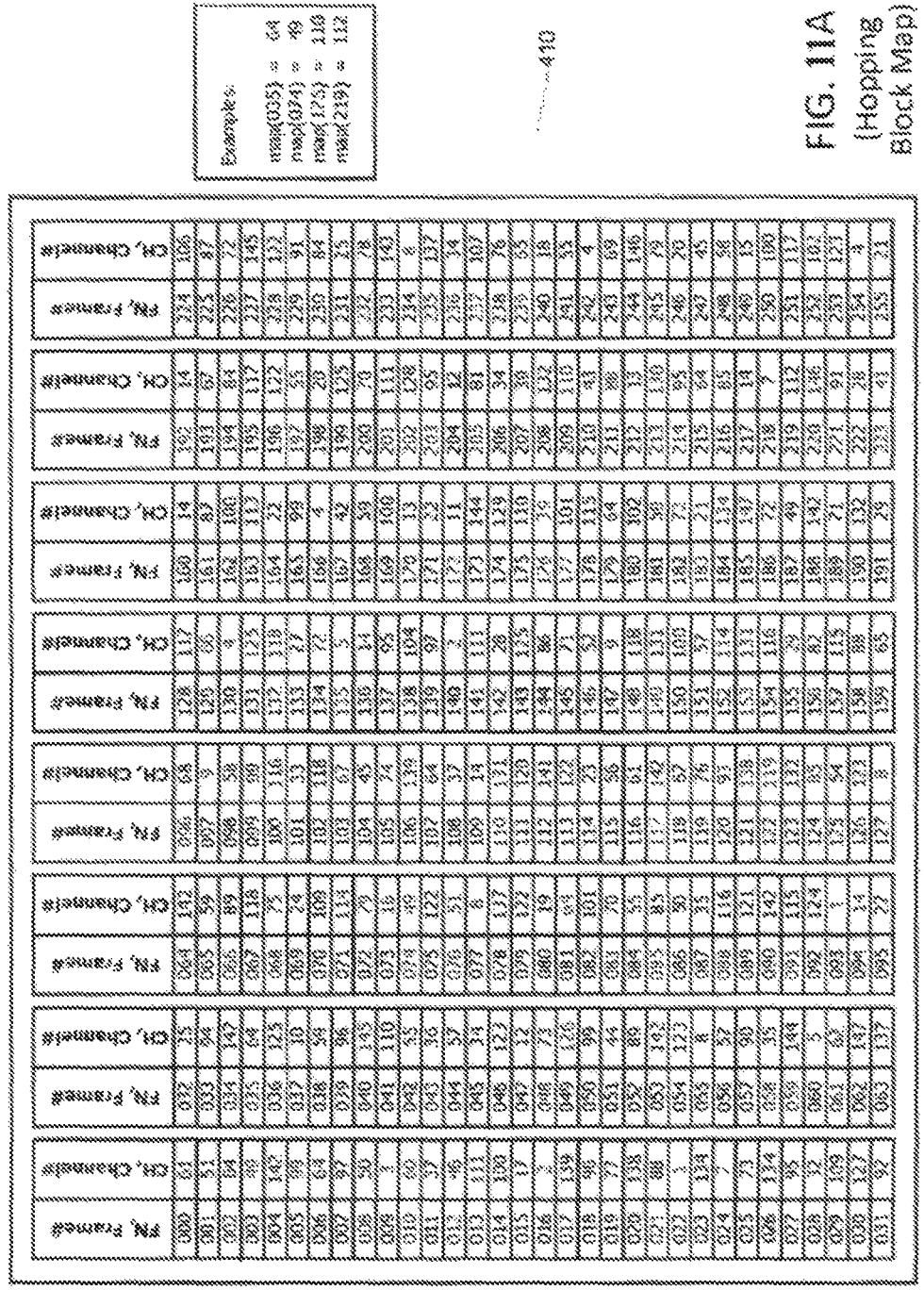
FIG. 11A (Hopping Block Map)

FIG. 11B (Hopping Block Schedule)

REAL-TIME ASSET LOCATION SYSTEM AND METHOD WITH LONG-RANGE WIRELESS BACKHAUL

FIELD OF THE DISCLOSURE

Embodiments of the present invention relate to systems and methods of tracking the location objects or otherwise receiving information via a short-range wireless protocol and relaying that information via a different long-range wireless protocol for further processing.

BACKGROUND

In a myriad of applications, there is a need to identify the location of an object. One example of such an application is a hospital environment. One example of an object to be tracked in a hospital environment is a mobile hospital bed.

Some hospital beds are mounted on wheels. This enables the hospital bed to be transported from one location to another location. In some instances, the movement of the hospital bed from one location to another location occurs when the hospital bed is unoccupied. The unoccupied movement of a hospital bed could occur, for example, when the tasking of a given room in a hospital is permanently, or temporarily, revised. Later, perhaps much later, further movement of the unoccupied hospital bed may be desired. For example, upon the conclusion of a temporary re-tasking of several hospital rooms, it may be desired to return a large number of unoccupied hospital beds to their original locations.

However, absent an automated system for tracking the location of each and every hospital bed, the location of one or more unoccupied hospital bed(s) may have become unknown. For example, a human error in accurate record keeping could render the location of one or more unoccupied mobile hospital beds unknown. In another example, an unoccupied mobile hospital bed may have been further moved in the interim to provide facility access for an unrelated cleaning or maintenance operation, and not returned to its recorded location upon conclusion of the unrelated facility cleaning or maintenance.

In other instances, the movement of a hospital bed from one location to another location occurs when the hospital bed is occupied. The occupied movement of a hospital bed may occur, for example, in situations where it is medically undesirable to remove the patient from the bed. For example, an occupied mobile hospital bed may be moved from a patient's assigned room to a different room in the hospital to perform a surgical or other medical procedure. Later, upon improvement or other fundamental change in the status of the patient's condition, the patient might be further transported from one location in the hospital to another location in the hospital by wheelchair, leaving the hospital bed behind. In such instances, a system for knowing the location of the patient would be inadequate to know the location of the mobile hospital bed.

Accordingly, there is a need for a system and method to know the location of mobile hospital beds in real time. The foregoing example applies similarly in other applications. For example, it is well known that merchants and manufacturers have a need and corresponding desire to track the location of inventory that may be relocated from one location to another location within the facility of the merchant or manufacturer. It should be apparent that there are many other applications where there is a desire and benefit for a system and method for tracking the location of one or more objects.

One approach to implementing a system and method for tracking objects utilizes a location information collector, sometimes also called a reader (or collector, for short), to communicate location information upstream in the system through a physical wire or cable such as electrically conductive wire or fiber optic cable. Such a system could be implemented in a hospital, a warehouse or other manufacturing facility, or in a brick and mortar retail store. However, such systems are intrusive. A physically wired and/or cabled system for tracking objects requires the installation of physical wires and/or cables throughout the facility coverage area in order for the location information to be transmitted upstream from the collectors. This results in a considerable expense of materials and time consuming labor.

Further, there is a need and desire for a system and method of tracking the location of one or more objects in other applications where the installation of wiring and/or cabling upstream from the collectors or readers is not practical. For example, there is a need and desire for a system and method of tracking the location of workers at a construction site, including a construction site not yet sufficiently developed to have wiring and/or cabling installed.

In other examples, there is a need and a desire for a system and method of tracking the location of workers in greenhouses and other agricultural environments. In these and many other applications, the location of the object desired to be tracked is sufficiently remote from any necessary infrastructure, and/or sufficiently distributed, such as in an agricultural field of dozens or even hundreds of acres, that the hard wiring of wires or cables to transmit information upstream from the collectors in a location tracking system and method is not practical. In such sufficiently remote and/or distributed applications, a requirement of wires and/or cables to transmit information upstream from the collectors prevents the need and desire for a system to track the location of objects from being satisfied.

Even the provision of electrical wires as a source of power to operate the collectors in the system is impractical in some applications. An agricultural environment distributed over a large outdoor area is an example of once such an application. Another example is low level product location tracking in a large lumber yard.

Accordingly, there is a need for a system that tracks the location of one or more objects where the collectors in the system are not connected to any other component in the system by any wiring. In a corresponding manner, there is a need for a method of tracking the location of one or more objects where the collectors in the system not only receive signals from the tracked objects wirelessly, but also communicate with upstream components in the system only wirelessly.

Returning to the example of the hospital environment, wireless communication from the collectors to upstream components, such as access points, in an object tracking system and method, potentially present additional concerns. For example, in current hospital environments a lot of information unrelated to tracking the location of objects is also communicated wirelessly via an existing wireless hospital network. Thus, wireless communication from collectors to upstream components such as access points in an asset tracking system and method in a hospital that communicate by way of an existing wireless hospital network would reduce the available bandwidth for other communications in that network and would require involvement of IT professionals to coordinate the coexistence of these communications with other communications using that existing wireless hospital network. Thus, there is a need for an object tracking system and method that communications wirelessly from collectors to upstream components by way of a wireless network that is entirely separate and discrete from other wireless network communications that are operating in the same space.

For applications where even the provision of hard wired electrical power for operating the collectors is impractical, as discussed above, there is a need for a system and method for tracking the location of objects where the collectors are battery powered. It is well known that, in devices that are battery powered, the rate of power consumption is a concern. Accordingly, for systems and methods of tracking the location of objects utilizing battery powered collectors, there is a need that the collectors consume little power in order to stay operational over long periods of time.

The foregoing also applies to situations where the information transmitted through, and processed by, the system is information other than the location of an asset. For example, in various embodiments the information can exclusively, or additionally, include any one or combination of: a temperature reading from a temperature sensor, a meter reading from a meter such as a utility usage meter, an indication of the presence or absence of a condition such as a door being open or closed, a/the door being locked or unlocked, and/or presence or absence of a harmful gas, and so on. Other examples include where the object is a consumable dispenser such as a paper towel dispenser and/or a soap dispenser and the information transmitted from the object includes a usage event related to usage of the consumable dispensed by the dispenser. Examples of such usage events include an amount of the consumable dispensed, a time during which dispensing of the consumable occurred, and a time when the dispenser is opened and the consumable changed or replaced.

SUMMARY

It is to be understood that both the following summary and the detailed description are exemplary and explanatory and are intended to provide further explanation of the present invention as claimed. Neither the summary nor the description that follows is intended to define or limit the scope of the present invention to the particular features mentioned in the summary or in the description. Rather, the scope of the present invention is defined by the appended claims.

In certain embodiments, the disclosed embodiments may include one or more of the features described herein.

Embodiments overcome the deficiencies in other approaches described above. Thus, various embodiments include systems and methods for tracking the location of one or more objects wherein the collectors communicate upstream wirelessly. Various embodiments include systems and methods for communicating a temperature reading from a temperature sensor, a meter reading from a meter such as a utility usage meter, an indication of the presence or absence of a condition such as a door being open or closed, a/the door being locked or unlocked, and/or presence or absence of a harmful gas. Various embodiments include systems and methods for communicating consumables usage events such as an amount of the consumable dispensed, a time during which dispensing of the consumable occurred, and a time when the object is opened and the consumable changed or replaced where the object is a consumable dispenser.

Various embodiments implement the wireless communication from the collectors to upstream components using a wireless network separate and discrete from other wireless network(s) operating in the area. In various embodiments, the foregoing separate and discrete wireless network is implemented such that the communication thereon is completely "air gapped" from wireless communications on other wireless networks in the environment. Various embodiments include systems and methods for tracking the location of one or more objects wherein the collectors are battery powered. And, in a corresponding manner, various embodiments operate in a wide-area network and/or under low power. As all of the communication is wireless, as the collectors and access points communicate via a low power protocol, various embodiments the invention described herein are entirely battery powered and wireless.

It is believed that embodiments with a collector that is entirely wireless, both for data communication and power, cost less than ten percent as much to install as a comparable system with wired connections for both power and upstream communication from the collector to the system access points. Likewise, in embodiments where the wireless communication from the collectors to upstream components occurs on a wireless network that is entirely separate and discrete from any wireless network used for other wireless communications in the environment, it is believed that the need to involve system administrators and/or information technology professionals in connection with approval(s) and installation of the system is dramatically reduced or even eliminated.

As detailed herein, the components of exemplary embodiments can be entirely wireless and battery powered. Thus, the readers operating on battery power can be located, for example, on an iron I-beam such that they are within range of beacons sent from the physical person of a construction worker to sense whether a given construction worker is on his job site as expected. The gateway(s) can be located in a safe housing at the base of a building under construction; and, all communications between the readers and the gateway(s), and all communications upstream from the gateway(s), is performed wirelessly. Using the agricultural example, in embodiments of the invention described herein, collectors and access points can be installed on telephone poles, lighting housings, or even secured to a naturally occurring object such as a tree in a field containing no fixed man-made objects of any description.

Accordingly, an aspect of the present invention provides a system for transmitting information using two different wireless communication protocols, the system comprising: an object including a short range radio frequency signal transmitter for transmitting a signal using a first wireless communications protocol, the signal including information transmitted from the object; a collector within a short range radio frequency signal range of the object, the collector including a signal receiver for receiving the signal transmitted by the short range radio frequency transmitter using the first wireless communications protocol, the collector further including a collector transmitter that transmits a collector signal using a second wireless communication protocol via a low power wide area network, the collector signal including the information transmitted from the object; a gateway in wireless communication with the collector via the low power wide area network, the gateway including a gateway receiver for receiving the collector signal; a processing application for processing the information transmitted from the object and creating an information processing outcome; and an end user terminal having an interface for displaying the information processing outcome.

In a specific implementation of the foregoing, an aspect of the present invention provides a system for identifying the location of one or more objects in real time, the system comprising: an object such as a hospital bed located in a hospital, or a human laborer located in an agricultural field or at a construction site, the object including a short range radio frequency signal transmitter for transmitting a signal with unique information that is associated with, and thereby identifies, the object using a first wireless communications protocol; a collector within a short range radio frequency signal range of the object, the collector including a signal receiver for receiving the signal with unique information that is associated with, and thereby identifies, the object using the first wireless communications protocol, the collector further including a transmitter for transmitting a signal including the unique information that is associated with the object using a second wireless communication protocol via a low power wide area network; a gateway in wireless communication with the collector via the low power wide area network, the gateway including a receiver for receiving the signal with information including the unique information that is associated with the object from the collector; a processing application for processing the information, including determining the association between the unique information and the object thereby identified, and creating an information processing outcome; and an end user terminal having an interface for displaying the information processing outcome. In various embodiments, the collector is battery powered.

Another aspect of the present invention provides a method of determining the location of one or more objects, comprising: sending a beacon advertisement message from an object to a collector via a first wireless communications protocol, the first wireless communications protocol being a short range radio frequency communications protocol, the beacon advertisement message including a unique MAC address; processing the information at the collector, thereby creating a collector processing result; sending the collector processing result from the collector to a gateway via a second wireless communications protocol, the second wireless communications protocol being a low power wide area network communications protocol; relaying the collector processing result from the gateway to one or more upstream components; further processing the collector processing result, thereby determining that the unique MAC address corresponds to the object and creating a location identification processing result, the location identification processing result identifying the location of the object; and displaying the location identification processing result on an end user terminal. In various embodiments, the second wireless communications protocol is a chirp spread spectrum radio modulation format that transmits the collector processing result over a long range between the collector and the gateway according to one or more of the many details thereof described herein.

BRIEF DESCRIPTION OF THE DRAWINGS

The accompanying drawings, which are incorporated herein and form a part of the specification, illustrate exemplary embodiments and, together with the description, further serve to enable a person skilled in the pertinent art to make and use these embodiments and others that will be apparent to those skilled in the art. Embodiments of the present invention will be more particularly described in conjunction with the following drawings wherein:

FIG. 11A is a particular implementation example of a frequency-block hopping map (which itself is a species of a frequency-block hopping guide), according to an embodiment of the present invention;

FIG. 11B is a particular implementation example of frequency-block hopping schedule (which itself is a species of a frequency-block hopping guide), according to an embodiment of the present invention;

DETAILED DESCRIPTION

Figure 1:
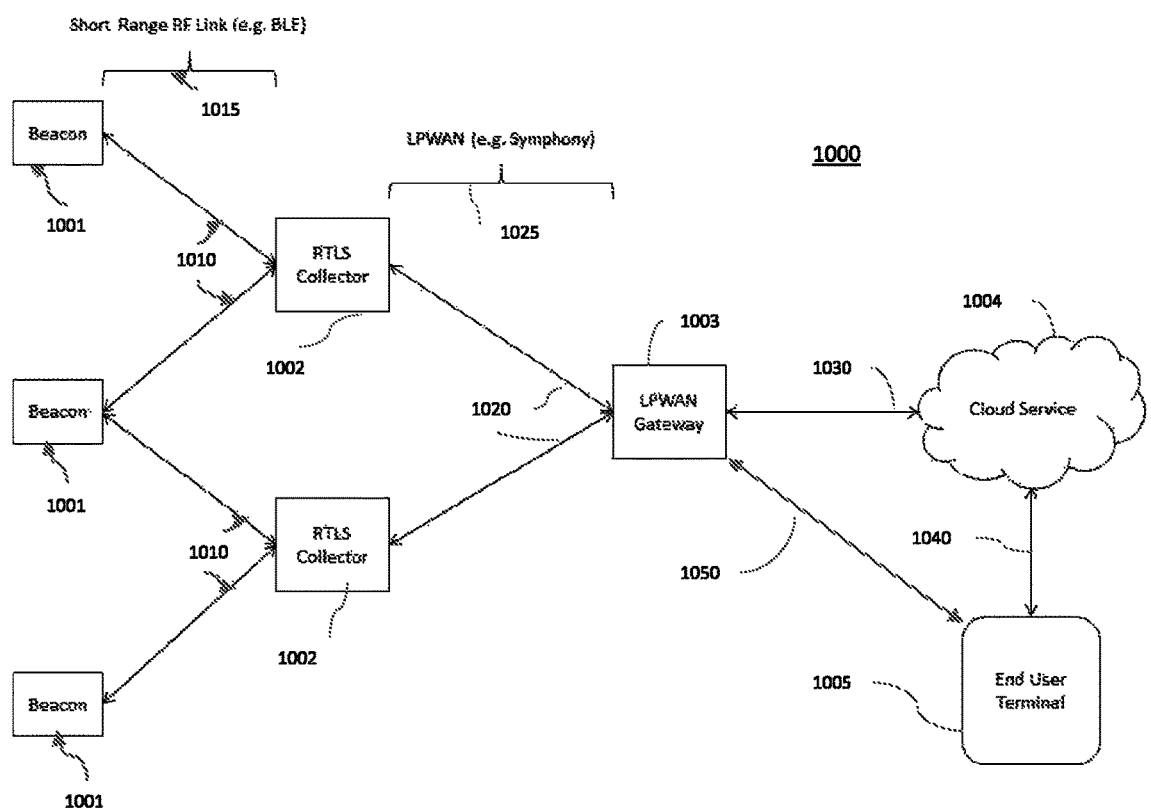
FIG. 1 is a block diagram of a system according to an embodiment of the present invention.

Embodiments of the present invention will now be disclosed in terms of various exemplary embodiments. This specification discloses one or more embodiments that incorporate features of the present invention. The embodiment(s) described, and references in the specification to "one embodiment", "an embodiment", "an example embodiment", etc., indicate that the embodiment(s) described may include a particular feature, structure, or characteristic. Such phrases are not necessarily referring to the same embodiment. The skilled artisan will appreciate that a particular feature, structure, or characteristic described in connection with one embodiment is not necessarily limited to that embodiment but typically has relevance and applicability to one or more other embodiments.

In the several figures, like reference numerals may be used for like elements having like functions even in different drawings. The embodiments described, and their detailed construction and elements, are merely provided to assist in a comprehensive understanding of the present invention. Thus, it is apparent that the present invention can be carried out in a variety of ways, and does not require any of the specific features described herein. Also, well-known functions or constructions are not described in detail since they would obscure the present invention with unnecessary detail.

The description is not to be taken in a limiting sense, but is made merely for the purpose of illustrating the general principles of the present invention, since the scope of the present invention is best defined by the appended claims.

It should also be noted that in some alternative implementations, the blocks in a flowchart, the communications in a sequence-diagram, the states in a state-diagram, etc., may occur out of the orders illustrated in the figures. That is, the illustrated orders of the blocks/communications/states are not intended to be limiting. Rather, the illustrated blocks, communications, and/or states may be reordered into any suitable order, and some of the blocks/communications/states could occur simultaneously.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items. As used herein, the singular forms "a", "an" and "the" are intended to include the plural forms as well, unless the context clearly indicates otherwise.

The word "exemplary" is used herein to mean "serving as an example, instance, or illustration." Any embodiment described herein as "exemplary" is not necessarily to be construed as preferred or advantageous over other embodiments. Additionally, all embodiments described herein should be considered exemplary unless otherwise stated.

The word "network" is used herein to mean one or more conventional or proprietary networks using an appropriate network data transmission protocol. Examples of such networks include, PSTN, LAN, WAN, WiFi, WiMax, Internet, World Wide Web, Ethernet, other wireless networks, and the like.

The phrase "wireless device" is used herein to mean one or more conventional or proprietary devices using radio frequency transmission techniques. Examples of such wireless devices include cellular telephones, desktop computers, laptop computers, handheld computers, electronic games, portable digital assistants, MP3 players, DVD players, or the like.

FIG. 1 is a block diagram of a system according to an embodiment of the present invention. Referring to FIG. 1, in a preferred embodiment, the Figure illustrates an embodiment of a real-time location services ("RTLS") System 1000 according to the invention. However, as mentioned above and detailed below, various embodiments of the system include other functionalities that are not asset tracking; and, certain embodiments do not include asset tracking. On the left in FIG. 1 are illustrated three objects 1001 being tracked by the system 1000. These three objects 1001 are represented by boxes containing the word "Beacon." This is because, in embodiments, the objects 1001 transmit a beacon 1010 to broadcast or announce their presence. It should be apparent that, in various embodiments, any number of assets 1001 exist. This includes, potentially, not only embodiments that track hundreds, thousands, and even more assets 1001, but also, potentially, embodiments that track a single asset 1001.

In embodiments, the foregoing is achieved by attaching a short range, radio frequency (RF) device to the object being tracked 1001. In embodiments, this short range RF device is battery powered.

It is assumed that the object being tracked 1001 has a value. Thus, throughout this description, the term "asset" may be used interchangeably with and for the phrase "object being tracked," or, "object" for short. In other embodiments, as described elsewhere herein, the "object" is a sensor rather than an asset having a location that is being tracked. Nevertheless, it should be understood that all of these terms are intended to be understood as being interchangeable herein. Thus, in any instance where the term "asset" is used herein, the reader should understand that the description thereof also applies where the "asset" is, instead, a sensor transmitting (a) sensor reading(s)/data. For example, as described elsewhere herein, in some embodiments the object is a consumables dispenser. Further, it although the inanimate terms object and/or asset are used herein for the object being tracked 1001, as discussed elsewhere herein it should be understood that the object being tracked 1001 is, in certain applications, a living creature such as a human being, such living creatures also having value.

The RF device attached to the asset 1001 is, in some embodiments, an RFID tag. In other embodiments, the RF device attached to the asset 1001 is a Bluetooth (BT) tag. In certain embodiments, in order to achieve a low power consumption, the RF device attached to the asset 1001 is a low power device. Accordingly, in certain embodiments, the transmission range of the RF device attached to the asset 1001 is a short range. RFID and BT tags are examples of such low power devices with a limited transmission range.

The beacons 1010 transmitted by the RF device attached to each asset 1001 identify each asset 1001 with unique identification information such as a unique MAC address. Thus, the system 1000 is able to process that information to understand specifically which asset 1001 is being identified by the beacon 1010 transmitted by the RF device attached to that asset 1001.

In various embodiments, the object 1001 is a sensor that transmits a signal. As mentioned above, examples include embodiments where the object 1001 is a temperature sensor and the signal 1010 is a signal that includes an indication of a temperature at the location of the object 1001. In other examples, the object 1001 is a meter and the signal 1010 is a signal that includes an indication of a reading by the meter, such as gas, electric or water utility usage, or the like. In still other examples, the object 1001 is a door and the door includes one or more sensors that sense whether the door is open or closed and/or whether the door is locked or unlocked. In such embodiments, the signal 1010 includes an indication whether the door is locked or unlocked and/or whether the door is closed or open. Still further, as also discussed elsewhere herein, in various embodiments the object 1001 is a consumables dispenser such as a paper towel dispenser or a liquid hand soap dispenser and the signal 1010 is a signal that indicates a usage event related to usage of the consumable dispensed by the dispenser. Examples of such usage events include an amount of the consumable dispensed, a time during which dispensing of the consumable occurred, and a time when the dispenser is opened and the consumable is changed or replaced.

In still other embodiments, the object 1001 is a gas detector that detects the presence of a toxic gas above a predetermined concentration level, such as a concentration level that presents a health risk upon exposure to humans. In such embodiments, the signal 1010 is a signal that includes an indication whether the object 1001 is presently detecting a given gas above a predetermined concentration level. Such embodiments could be used merely for triggering an alarm condition. Such embodiments can also be implemented such that the signal 1010 indicates the concentration level and the processing of that reading occurs upstream. It should be apparent that the foregoing does not constitute an exhaustive list of embodiments where the object 1001 is other than an asset having a location to be tracked.

One example of the nature of the short range RF link 1015 between the asset(s)/object(s) 1001 and the RTLS Collector(s) 1002 by which the beacon(s)/signal(s) 1010 are transmitted is Bluetooth Low Energy (BLE), the standard for BT communication upstream from a BT device such as a BT tag. However, it should be apparent that any currently known, or later developed, technology for sending a signal that identifies an asset can be implemented in embodiments. To the right of the assets in FIG. 1, two RTLS Collectors (or, "collectors" for short) 1002 are shown. It should be apparent that, in various embodiments, any number of RTLS Collectors 1002 are utilized. The number of RTLS Collectors 1002 in any given system is a design function of the area of coverage for that particular implementation of the system 1000.

The lines connecting respective assets 1001 with respective collectors 1002 indicate that those particular assets 1001 are within sufficient proximity with those particular collectors 1002 so as to establish communication there-between. The double-sided arrows on the lines connecting respective assets 1001 with respective collectors 1002 indicate that each asset 1001 and each collector 1002 are capable of bi-directional communication there-between.

It is believed to be preferable (though not necessary required) that every asset 1001 in an RTLS System 1000 be capable of communication with, and thus in sufficient proximity to, at least one RTLS Collector 1002 at all times that the asset 1001 is within the system 1000. In order to achieve such an implementation, it may be necessary that some overlap exist between the short range communication ranges in which each RTLS Collector 1002 is able to read a beacon signal 1010 sent by any given asset 1001. Accordingly, when an asset 1001 is in such an area of overlap, the beacon 1010 sent by that asset 1001 will be readable (and read) by plural RTLS Collectors 1002. This is true of the asset 1001 in the center of the three assets 1001 in FIG. 1. As depicted, that central asset 1001 is in communication with both of the RTLS Collectors 1002 depicted in the Figure.

The RTLS Collectors 1002 relay the data received in beacon signals 1010 from the assets 1001 upstream. In the depicted embodiment, a single low-power wide-area network (LPWAN) Gateway 1003 is the upstream device that receives the signals 1020 sent upstream by the RTLS Collectors 1002. However, in various embodiments, plural LPWAN Gateways 1003 are implemented. The number of LPWAN Gateways 1003 in any given embodiment is a design parameter of that particular implementation of the system 1000. Elsewhere herein, an LPWAN Gateway 1003 is also referred to as an Access Point (AP).

In order for the system to operate, each RTLS Collector 1002 must be within range of at least one LPWAN Gateway 1003. Thus, in the depicted embodiment, both RTLS Collectors 1002 are within range of the LPWAN Gateway 1003 as indicated by the lines connecting the LPWAN Gateway 1003 to each respective RTLS Collector 1002. The bi-directional arrows on these lines indicate that communication between each RTLS Collector 1002 and the LPWAN Gateway 1003 is bi-directional communication.

The signals 1020 relayed upstream from the RTLS Collectors 1002 to the LPWAN Gateway(s) 1003 are long range LPWAN wireless signals. As discussed elsewhere herein in greater detail, the wireless nature of these signals 1020 eliminates the need for a hard wired backhaul communications network between the Collectors 1002 and the Gateway(s) 1003. And, as also discussed elsewhere herein in greater detail, in certain embodiments, the RTLS Collectors 1002 operate on a sufficiently low power so as to be battery powered where desired. As such, in certain embodiments, the RTLS Collectors 1002 have no wired connections of any sort.

In various embodiments, the RTLS Collectors 1002 are easily, movable, removable and replaceable. This is particularly true of embodiments where the RTLS Collectors 1002 have no hard wired connections of any sort. And, in embodiments where the RTLS Collectors 1002 are easily movable, removable and replaceable, the system 1000 has far greater flexibility to adapt to changing needs of the application and to continue operating with minimal interruption when a given RTLS Collector 1002 needs to be repaired or replaced.

Further, as discussed elsewhere herein in greater detail, the LPWAN backhaul network 1025 is of such a nature that, in certain embodiments, it operates on a wireless network that is completely separate and discrete from any existing wireless communications network implemented in parallel thereto. Such embodiments improve the security of any such parallel wireless communications network while also improving the security of the systems and methods according to the present invention.

Upon receiving the signals 1020 relayed thereto by the RTLS Collectors 1002, the LPWAN Gateway 1003 relays that RTLS data to the Cloud Service 1004 through a bi-directional Internet connection 1030, indicated by the bi-directional arrow 1030 between the Cloud Service 1004 and the LPWAN Gateway 1003. In certain embodiments, the Internet connection 1030 between the LPWAN Gateway 1003 and the Cloud Service 1004 is a cellular connection. In other embodiments, the Internet connection 1030 between the LPWAN Gateway 1003 and the Cloud Service 1004 is achieved by means other than a cellular connection.

In the depicted embodiment, the Cloud Service 1004 includes a remote application that aggregates and processes beacon data. This application performs the function(s) of associating the unique MAC address with the specific asset 1001 to which the unique MAC address corresponds, and identifying the location(s) of the asset(s) 1001. This application further performs whatever additional functions are desired and implemented in any particular asset location identification and tracking system.

Finally, the RTLS System 1000 depicted in FIG. 1 includes an End User Terminal 1005. In embodiments, the End User Terminal 1005 is in bi-directional communication 1040 with the Cloud Service 1004, as indicated by the bi-directional arrow 1040 connecting the End User Terminal 1005 and the Cloud Service 1004. In embodiments, the End User Terminal 1005 is in bi-direction communication 1050 with LPWAN Gateway 1003 such that there is not necessarily an intervening Cloud Service 1004 in the bi-directional communication 1050 between the End User Terminal 1005 and the LPWAN Gateway 1003.

In embodiments, the End User Terminal 1005 is implemented in any manner of interface with an end user. Examples of such an interface include an interface on a tablet or a personal computer (PC). In embodiments, the interface with the end user implemented in the End User Terminal 1005 enables the end user to perform whatever asset location and/or tracking function(s) a given asset tracking system is designed to enable. Likewise, in embodiments where one or more of the objects 1001 is a sensor rather than a tracked asset, the End User Terminal 1005 enables the end user to see the reading or result of the sensing by the sensor that is the object 1001. One example is identifying a particular asset 1001 and sending a command to locate that identified asset 1001. The system 1000 then, in real time, passes that command downstream to the RTLS Collectors 1002; and, the RTLS Collector(s) 1002 that are receiving the beacon 1010 from the identified asset 1001 pass that information back upstream to the user interface on the End User Terminal 1005. In an example where the object 1001 is a temperature sensor, the user can initiate an inquiry at the End User Terminal 1005 requesting a current temperature reading at the sensor 1001. In embodiments where the object is a consumables dispenser such as a paper towel or liquid hand soap dispenser, the user can initiate a query at the End User Terminal 1005 requesting a remaining amount of the consumable at the object 1001.

In embodiments, any number of plural End User Terminals 1005 are included as desired for any particular implementation of system 1000. Further, it should be understood that the described system is implemented, in various embodiments, to bridge one wireless communication protocol to another wireless communication protocol, and so on.

Figure 14:
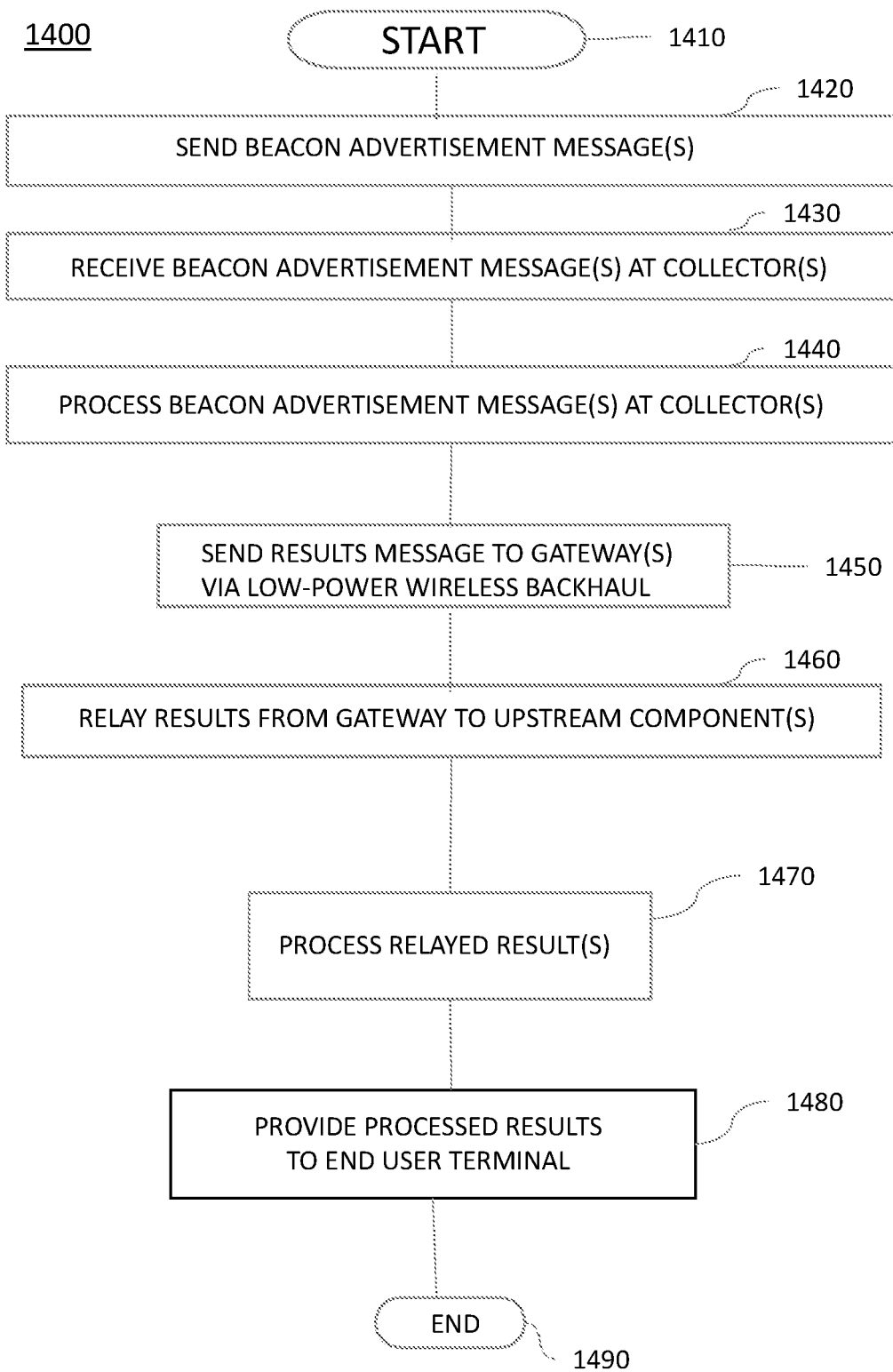
FIG. 14 is a flowchart illustrating a method according to an embodiment of the present invention.

According to the foregoing, referring now to FIG. 14, an exemplary method 1400 of using the foregoing RTLS System 1000 includes one or more of the following steps. First, the method 1400 begins at the start 1410. For the purpose of illustrating the method 1400 in a practical application, the application of the method in a hospital environment to track the location of a hospital bed identified by an RFID tag will be used.

The method 1400 then proceeds to step 1420. In step 1420, an asset beacon 1001 sends a "blind" advertisement message 1010. Using the example, an RFID tag attached to the hospital bed broadcasts its presence. It should be apparent that step 1420 is repeated for every beacon 1001 in the system 1000. In other words, in our example, every RFID tag attached to every hospital bed is broadcasting its presence in step 1420 of the method 1400.

The message 1010 contains unique identification (UID) data such as a unique MAC address that is subsequently processed to identify the asset 1001 from which that beacon 1010 is transmitted to the exclusion of all other assets or objects 1001. Accordingly, in our example, the signal 1010 transmitted by each RFID tag attached to each hospital bed 1001 includes a UID that identifies the specific hospital bed 1001 to which that RFID tag is attached. And, again, as described elsewhere herein, in embodiments where the object 1001 is a sensor rather than a tracked asset, the beacon advertisement messages of method 1400 are sensor readings.

The method 1400 then proceeds to step 1430, where each blind advertisement message 1010 is received by one or more respective RTLS Collector(s) 1002. In our example, an RTLS Collector 1002 is installed in each hospital room, perhaps in a corner of the wall and ceiling. It should be apparent that, in other examples, a collector 1002 need not be installed in every room. The RFID tag attached to the bed 1001 within the room sends the signal 1010 in step 1420. That signal 1010 travels wireless through the air and, in step 1430, the signal 1010 is received by the collector 1002 up by the ceiling.

Upon receiving the blind advertisement message(s) 1010 in step 1430, the method 1400 proceeds to step 1440. In step 1440, each collector 1002 processes each blind advertisement message 1010 received. In the processing of step 1440, for each blind advertisement message 1010 received, any given RTLS Collector 1002 measures a received signal strength (RSSI) of that blind advertisement message signal 1010 received. In embodiments, the collector 1002 also processes the UID to determine the particular asset 1001 identified by that UID. Accordingly, in our example, the collector 1002 knows which hospital bed 1001 is in that hospital room and, based on the RSSI, how far away from the collector is located that hospital bed 1001. It should be apparent that, in other examples the analysis of this information is not performed by the collector 1002 but rather is relayed upstream by the collector for processing by other components of the system 1000.

Accordingly, in other embodiments, the ability to identify the particular asset 1001 identified by a given UID is only implemented upstream of the collector 1002. However, it should be apparent that there are both advantages and disadvantages of embodiments where the ability to identify the particular asset 1001 identified by a given UID is not possible in step 1440. For example, an advantage of such an embodiment is that less processing ability need be implemented in each and every collector 1002. However, when a command to provide the location of a single particular asset 1001 is sent downstream to the collectors 1002 from the End User Terminal 1005, a disadvantage of embodiments where the collectors 1002 do not have the ability to process the UID in step 1440 so as to associate that UID with a specific asset 1001 is that every collector 1002 must reply by sending upstream every UID of every asset 1001 from which that collector 1002 is receiving beacon advertisement messages 1010.

In embodiments, the collector 1002 also processes the RSSI in step 1440 to more narrowly determine a specific location of the asset 1001. In embodiments, the collector 1002 implements and performs additional processing functionalities in step 1440. In embodiments, one or more of the functionalities implemented upstream in the Cloud Service 1004 and/or the End User Terminal 1005 is also and/or instead implemented in the collector 1002 and performed in step 1440.

Further, for each blind advertisement message received in step 1430, each RTLS Collector 1002 records a time stamp (TS) in step 1440, the TS specifying a time when the specified UID was received at the determined RSSI. Thus, in our example, the collector 1002 up by the ceiling of the hospital room makes a record that a UID was sensed within range on a particular date at a particular time.

The method 1400 then proceeds to step 1450. In step 1450, each RTLS Collector 1002 sends a results message 1020 to the LPWAN Gateway(s) 1003 with the UIDs and corresponding RSSIs and TSs noted in the signal processing of step 1440. The messages 1020 are sent from the collector(s) 1002 to the LPWAN Gateway(s) 1003 in step 1450 via a low power wireless backhaul according to the details described elsewhere herein. Accordingly, in our example, the collectors 1002 up by the ceilings of the hospital rooms wirelessly transmit the results message(s) 1020 via the LPWAN network to a centralized location in the hospital where an associated LPWAN Gateway 1003 is located. The could be, for example, in a computer server room.

The method 1400 then proceeds to step 1460. In embodiments of step 1460, the LPWAN Gateway 1003, in turn, sends a message 1030 to the Cloud Service 1004. Thus, in our hospital example, message 1030 is sent out of the hospital into the Internet cloud. In embodiments, the LPWAN Gateway(s) 1003 send(s) messages 1050 to the End User Terminal in step 1460. The message 1030 and/or the message 1050, sent by the LPWAN Gateway 1003 to the Cloud Service 1004 and/or the End User Terminal(s) 1005 in step 1460, relays all of the UIDs, RSSIs and TSs received from one or more of the collector(s) 1002 after being sent by the collector(s) in step 1450.

Using our hospital example, the End User Terminal 1005 would be located somewhere within the hospital. For example, the end user terminal 1005 could be located in the office of a hospital employee who has the responsibility of knowing where any given hospital bed 1001 is located. Thus, in embodiments where the message 1050 is sent directly from the LPWAN Gateway 1003 to the End User Terminal 1005, it can be possible to eliminate the need for communications over the Internet. Such an embodiment is capable of operating even when a connection to the Internet is unavailable, such as during an Internet service outage for example.

The method 1400 then proceeds to step 1470. In step 1470, the Cloud Service 1004 and/or the End User Terminal(s) 1005 then process(es) the results data received from the LPWAN Gateway(s) 1003 to determine the location of one or more of the asset(s) 1001. In embodiments where no signal 1050 is sent directly from the LPWAN Gateway(s) 1003 to the End User Terminal(s) 1005 in step 1460, all of the processing of the relayed results in step 1470 is performed in the Cloud Service 1004. In embodiments where signal 1050 is sent from the LPWAN Gateway(s) 1003 to the End User Terminal(s) 1005 in step 1460, and no signal 1030 is sent from the LPWAN Gateway(s) 1003 to the Cloud Service 1004 in step 1460, all of the processing of the relayed results in step 1470 is performed at the End User Terminal(s) 1005. In embodiments where both signal 1030 and signal 1050 are sent in step 1460, it should be apparent that the processing of step 1470 may be performed entirely by the Cloud Service 1004, entirely by the End User Terminal(s) 1005, or by any mixture of the Cloud Service 1004 and the End User Terminal(s) 1005.

Upon completion of the processing of the relayed results in step 1470, the method 1400 proceeds to step 1480. In step 1480, the processed results are provided to the End User Terminal(s) 1005. Thus, in our example, the hospital employee responsible for knowing the location of the hospital beds 1001 is able to learn those locations through a user interface on his or her electronic device.

In some embodiments where message 1030 is sent in step 1460, the Cloud Service 1004 sends a message 1040 to the End User Terminal in step 1480. In some embodiments, message 1040 is sent from the Cloud Service 1004 to the End User Terminal(s) 1005 immediately upon completion of the Cloud Service 1004 (portion of) processing in step 1470 of the message(s) 1030 received from the LPWAN Gateway(s) 1003 in step 1460. In some such embodiments, this message 1040 is sent immediately from the Cloud Service 1004 to the End User Terminal(s) 1005 in compliance with a system parameter established prior to completion of the Cloud Service 1004 processing in step 1470 of the message(s) 1030 received from the LPWAN Gateway(s) 1003 in step 1460. In other embodiments, the message 1040 is sent from the Cloud Service 1004 to the End User Terminal(s) 1005 after a delay following completion of the Cloud Service 1004 processing in step 1470 of the message(s) 1030 received from the LPWAN Gateway(s) 1003 in step 1460. In some such embodiments where the message 1040 sent from the Cloud Service 1004 to the End User Terminal(s) 1005 is delayed, the message 1040 is sent in step 1480 response to a query message sent from the End User Terminal 1005 to the Cloud Service 1004.

According to the foregoing description, is should be apparent that in some embodiments, the aggregation and beacon data processing application is located entirely in the Cloud Service 1004. However, in alternative embodiments, that functionality is located entirely in the End User Terminal(s) 1005. Advantages of locating this application entirely in the Cloud Service 1004 include reducing the cost and size of the End User Terminal(s) 1005. Further, in embodiments where multiple End User Terminals 1005 are included, locating the application in the Cloud Service eliminates what would otherwise be a need for redundancy in the application in the plural End User Terminals 1005. It should be apparent that, in embodiments where the application is located in the End User Terminal 1005, the End User Terminal 1005 is in direct bi-directional communication with the LPWAN Gateway 1003 via signal path 1050 by way of whatever intervening components or relays may exist.

In embodiments where some or all of the processing of step 1470 is performed by the End User Terminal 1005, the provision of the processed results in step 1480 is performed by way of communication internal to the End User Terminal 1005. Upon completion of step 1480, the method 1400 proceeds to step 1490 where the method 1400 ends.

Certain exemplary embodiments implementing the foregoing will now be described in detail. In connection with the following detail, it should be noted that the wireless network 100 discussed below corresponds to the communication between the LPWAN Gateway and the Cloud Service. It should also be noted that the wireless network 100, in the following detail, also corresponds to the communication between the End User Terminal and the Cloud Service in the system and method of determining the location of one or more objects in real time according to the embodiments described in detail below.

Similarly, it should be understood that, in connection with the exemplary system of FIG. 1, the instances of end node 102 described below correspond to the RTLS collector of the system and method for tracking the location of one or more objects in real time as depicted in FIG. 1. Likewise, it should be understood that instances of the central node 106 described below correspond to the LPWAN Gateway of the system and method for tracking the location of one or more objects in real time as depicted in FIG. 1.

Figure 2:
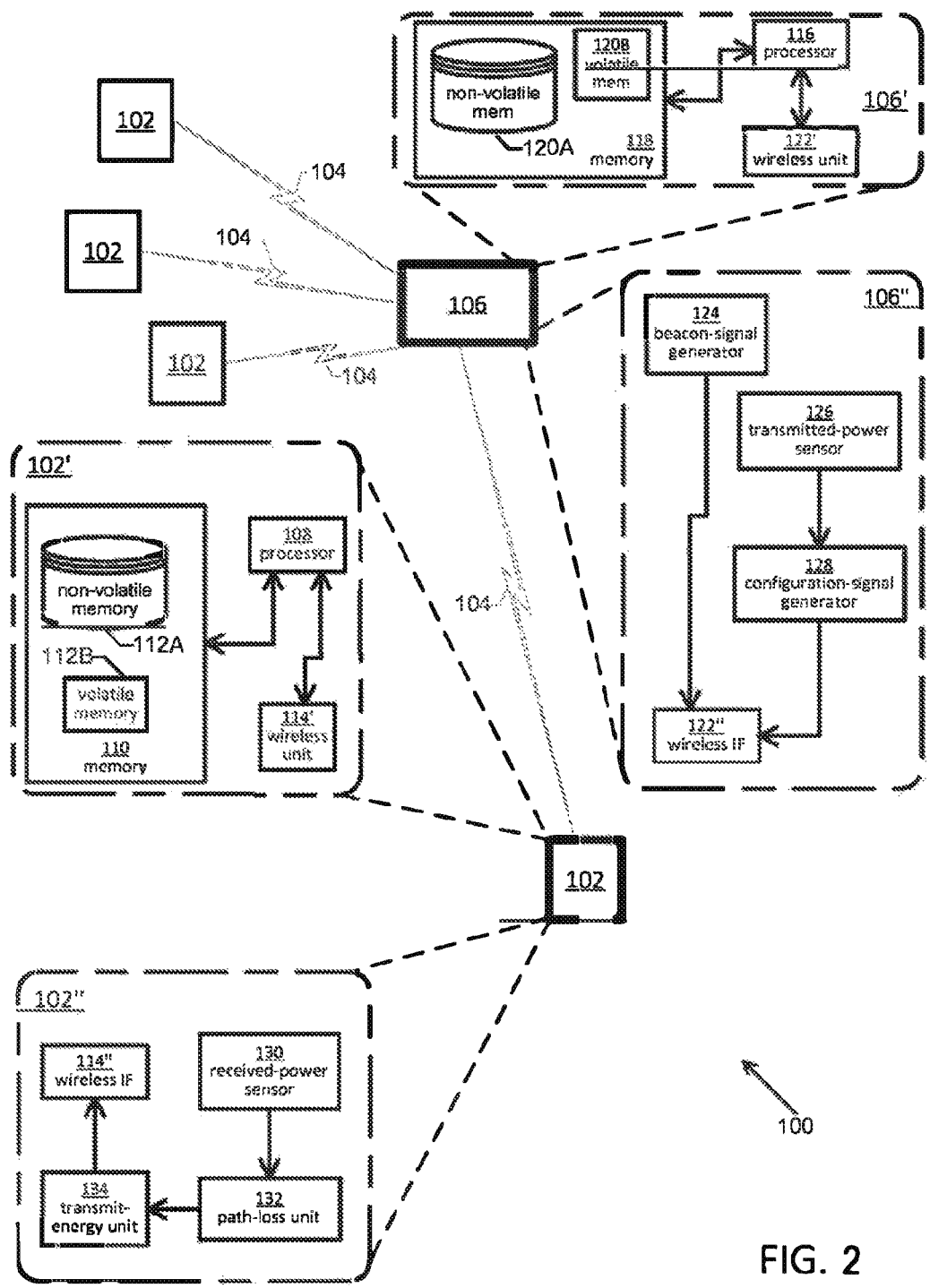
FIG. 2 is a block diagram of a wireless network, for example, a long-range, low-power network, according to an embodiment of the present invention, wherein FIG. 2 emphasizes physical unit and functional unit configurations.

FIG. 2 is a block diagram of wireless network 100, for example, a long-range, low-power network, according to an embodiment of the present invention, wherein FIG. 2 emphasizes physical unit and functional unit configurations.

In FIG. 2, wireless network 100 can be compatible with, e.g., the IEEE 802.15.4 standard, the LoRaWAN standard (as standardized by the LoRa™ Alliance), etc. For purposes of a more detailed discussion, at the physical layer, it will be assumed that wireless network 100 is compatible with the LoRa™ modulation format.

Network 100 includes: instances of end nodes 102; and a central node 106, e.g., a central gateway and/or a base station. Via wireless communication sessions 104, instances of end node 102 communicate with central node 106, respectively. As examples (and as will be discussed in more detail below, respectively), communications from central node 106 to instances of end node 102 can include a beacon signal and a configuration signal. Also as an example (and as will be discussed in more detail below), communications from an instance of end node 102 to central node 106 can include a data message. Accordingly, instances of end node 102 can be described as message-sourceable.

In terms of physical components (as illustrated by exploded view 102'), each instance of end node 102 includes: one or more instances of a processor 108; memory 110 which itself includes one or more instances of non-volatile memory 112A and one or more instances of volatile memory 112B; and a wireless unit 114'. Also, in terms of physical components (as illustrated by exploded view 106'), each instance of central node 106 includes: one or more instances of a processor 116; memory 118 which itself includes one or more instances of non-volatile memory 120A and one or more instances of volatile memory 120B; and a wireless unit 122'.

Each of wireless unit 122' and wireless unit 114' is configured to receive and transmit messages wirelessly, respectively. Overall, the physical components of central node 106 and of each instance of end node 102, respectively, are operable to engage in (among other things), e.g., LoRaWAN compatible, frequency modulated ("FM") chirp communication that is based on the generation of a stable chirp using a fractional-N ("fracN") phase-locked loop ("PLL") (the PLL not being illustrated). For example, the wireless transmissions can be performed in an unlicensed spectrum.

In terms of functional units (as illustrated by exploded view 102"), each instance of end node 102 includes: a received-power sensor 130; a path-loss unit 132; a transmit-energy unit 134; and a wireless interface 114". Also, in terms of functional units (as illustrated by exploded view 106"), central node 106 includes: a beacon-signal generator 124; a transmitted-power sensor 128; a configuration-signal generator 128; and a wireless interface 122". For each of central node 106 and a given instance of end node 102, such functional units can be implemented at least in part, e.g., as executable code stored in one or more of the memories thereof (noted above), with such code being executable by one or more of the processors (noted above), respectively. Such implementations can conform to the communication-layer diagram of FIG. 3 (discussed below).

Figure 3:
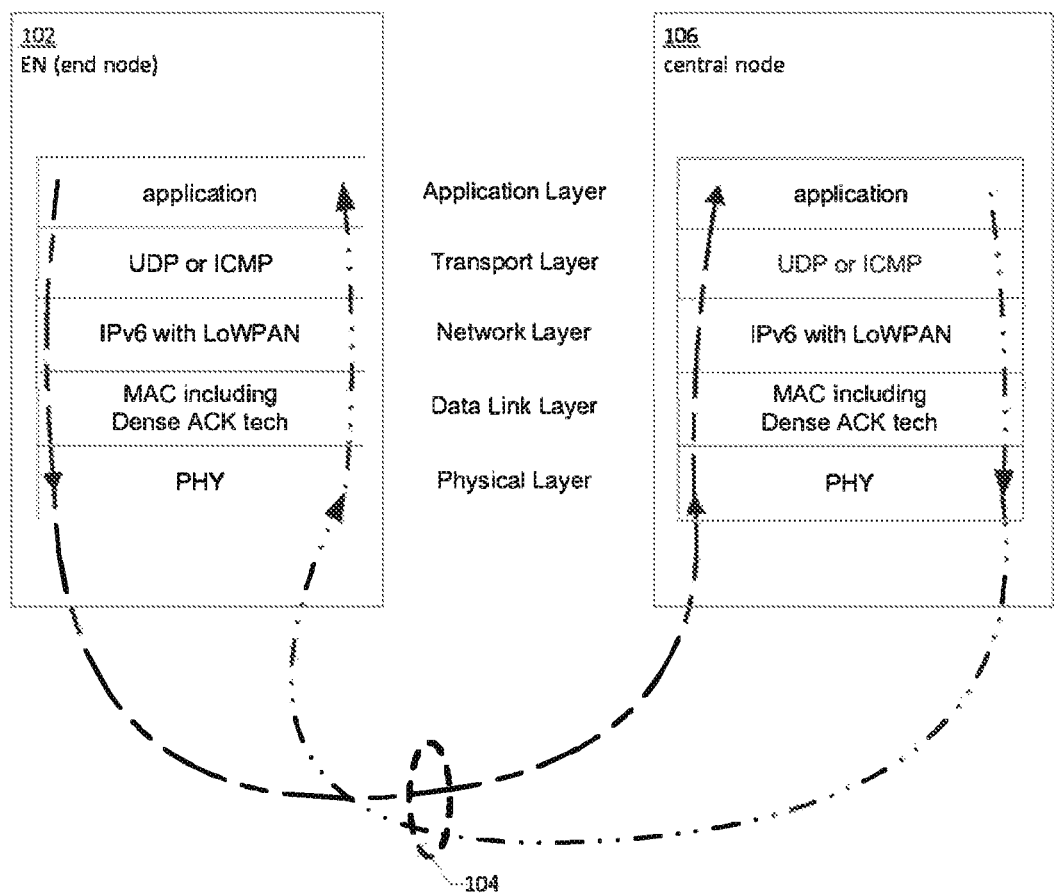
FIG. 3 is a communication-layer diagram illustrating the path of flow during an instance of a communication session between a central node and an instance of an end node, such as a collector, according to an embodiment of the present invention.

FIG. 3 is a communication-layer diagram illustrating the path of flow during an instance of communication session 104 between central node 106 and an instance of end node 102, according to an embodiment of the present invention.

Central node 106 and each instance of end node 102 can be implemented at least in part, e.g., as executable code stored in one or more of the noted (above) memories thereof and executed by one or more of the noted (above) processor units thereof, respectively. Such implementations can conform to the communication-layer diagram of FIG. 3.

More particularly, central node 106 and each instance of end node 102 can have a stack based (in part); on industry-standard layers. The layers illustrated in FIG. 3 represent but one example of combinations of layers that can be included in such stacks, respectively. Such layers, from bottom to top, for example (as illustrated in FIG. 3), can include: a physical layer; a data link (or MAC) layer that includes dense acknowledgement messaging-technology (see discussion below); a network layer (e.g., an IP with LoWPAN) layer; a transport layer (e.g., a UDP layer or ICMP layer); and an application layer. Alternatively, different combinations of layers could be used in the stack.

Figure 4:
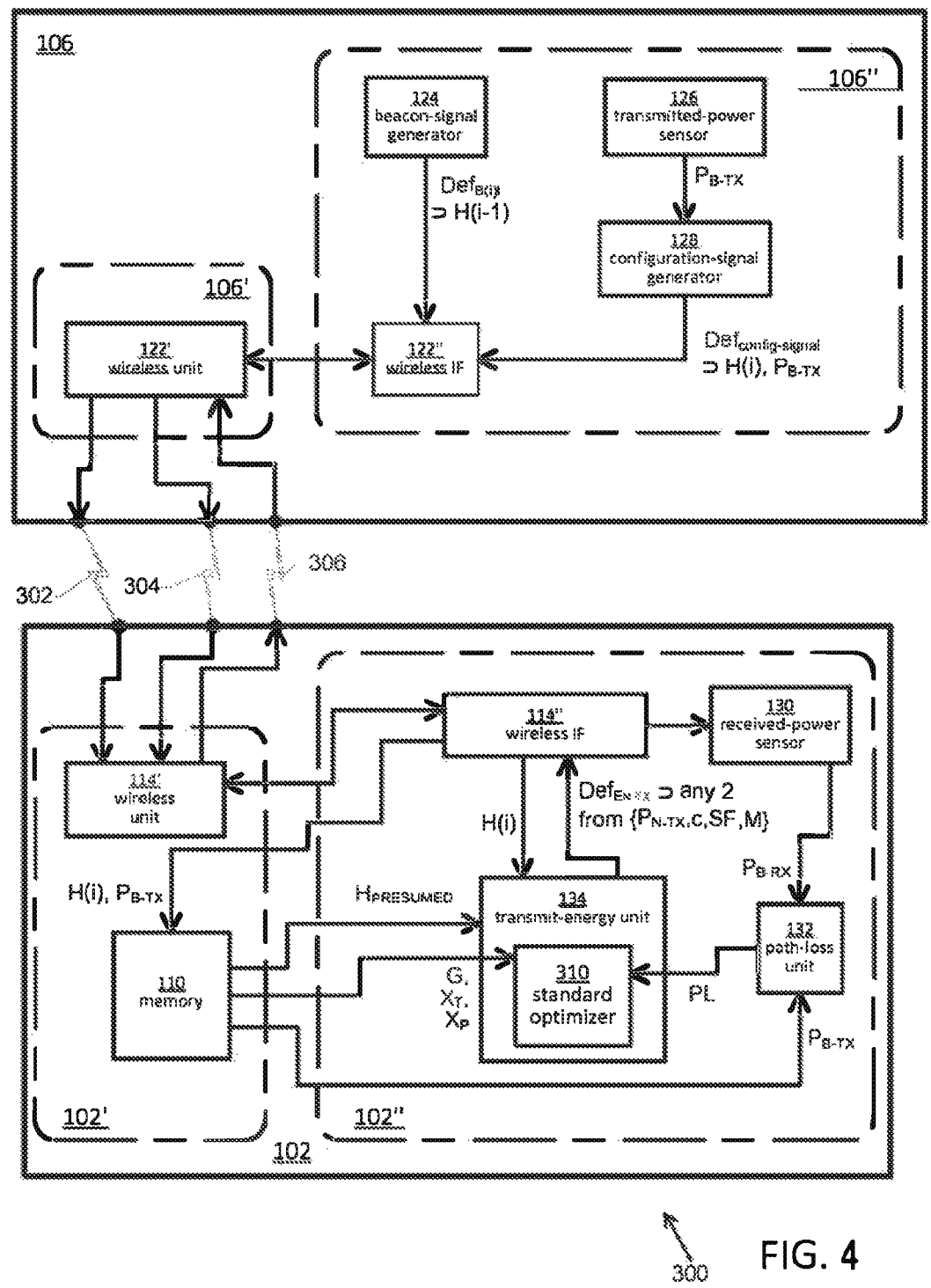
FIG. 4 is a block diagram illustrating a version of the wireless network of FIG. 2, according to an embodiment of the present invention, wherein FIG. 4 emphasizes signal flow.

FIG. 4 is a block diagram illustrating a version 300 of wireless network 100 of FIG. 2, according to an embodiment of the present invention, wherein FIG. 4 emphasizes signal flow. FIG. 4 will be discussed in the context of FIGS. 5A-5B and also in the context of FIGS. 6-7.

In FIG. 4, among other things, a standard optimizer 310 (discussed in more detail below) is illustrated as being included in transmit-energy unit 134; and instances 302, 304 and 306 of communication session 104 are illustrated. Briefly, central node 106 is configured, among other things, to: periodically generate and transmit a beacon signal B, which is illustrated in FIG. 4 as instance 302 of communication session 104; and periodically generate and send a configuration signal, which is illustrated in FIG. 4 as instance 304 of communication session 104. End node 102 is configured, among other things, to generate (as needed and/or as scheduled) a message to central node 106, the message being illustrated in FIG. 4 as instance 306 of communication session 104.

Wireless IF 122' is configured to periodically transmit, via wireless unit 122', as follows: the configuration signal at an interval, $I_{CONFIG}$; and the beacon signal at an interval, $I_{BEACON}$, wherein $I_{BEACON} < I_{CONFIG}$. For example, $I_{CONFIG} = 15*(I_{BEACON})$, e.g., $I_{CONFIG} = 30$ seconds and $I_{BEACON} = 2$ seconds. Also, for example, though the beacon signal is transmitted in an unlicensed spectrum, the beacon signal can be of sufficient bandwidth that it does not have to hop, i.e., it can be a non-hopping signal and yet be can be transmitted permissibly in the unlicensed spectrum because it is of sufficient bandwidth. As yet a further example, end node 102 can be configured to wirelessly transmit, at most, only one message therefrom corresponding to a given instance of the beacon signal.

Figure 5A:
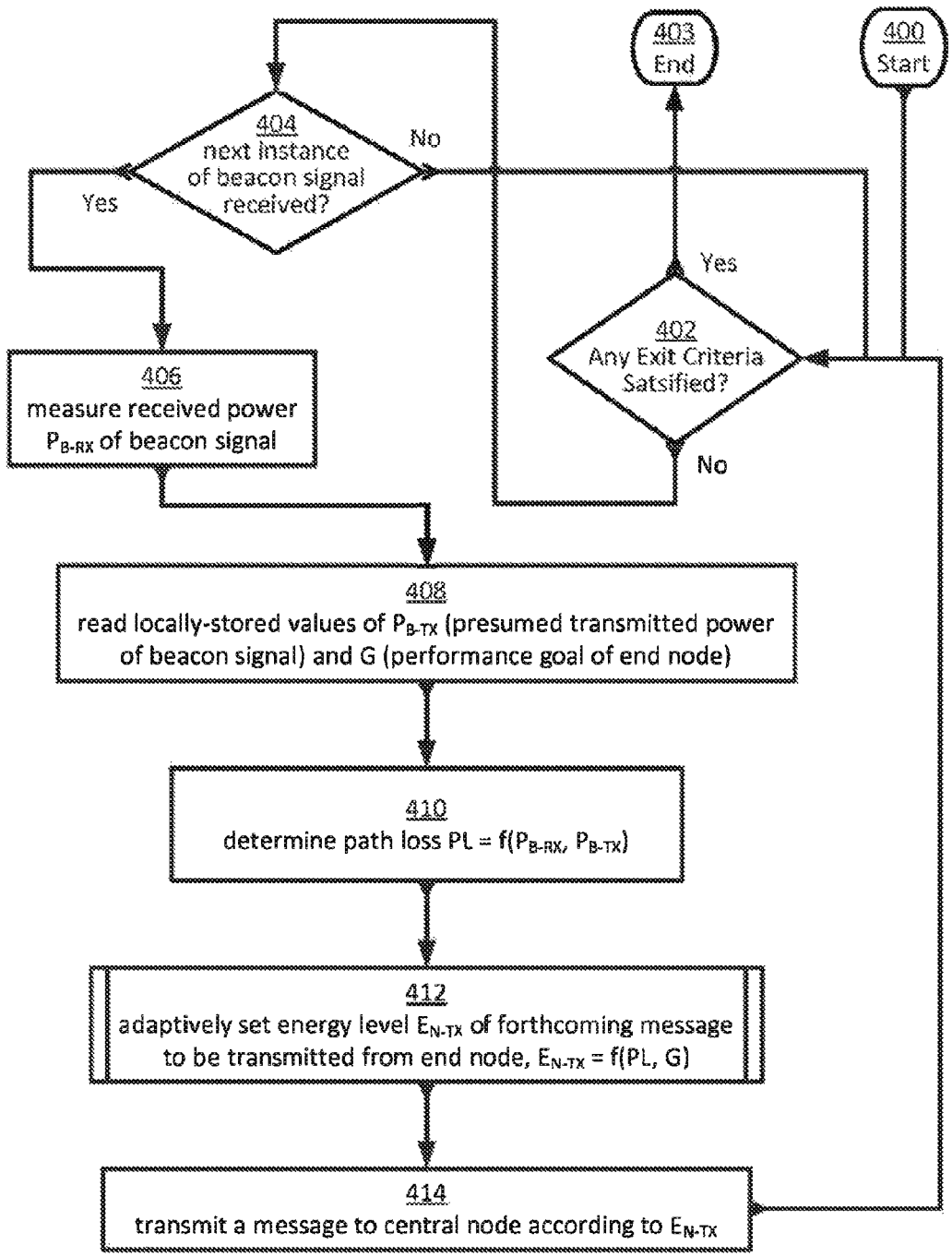
FIGS. 5A-5B are flowcharts illustrating a method of operating an instance of the end node, such as a collector, to wirelessly communicate with the central node, according to an embodiment of the present invention, with FIG. 5B illustrating one of the blocks of FIG. 5A in greater detail.
Figure 5B:
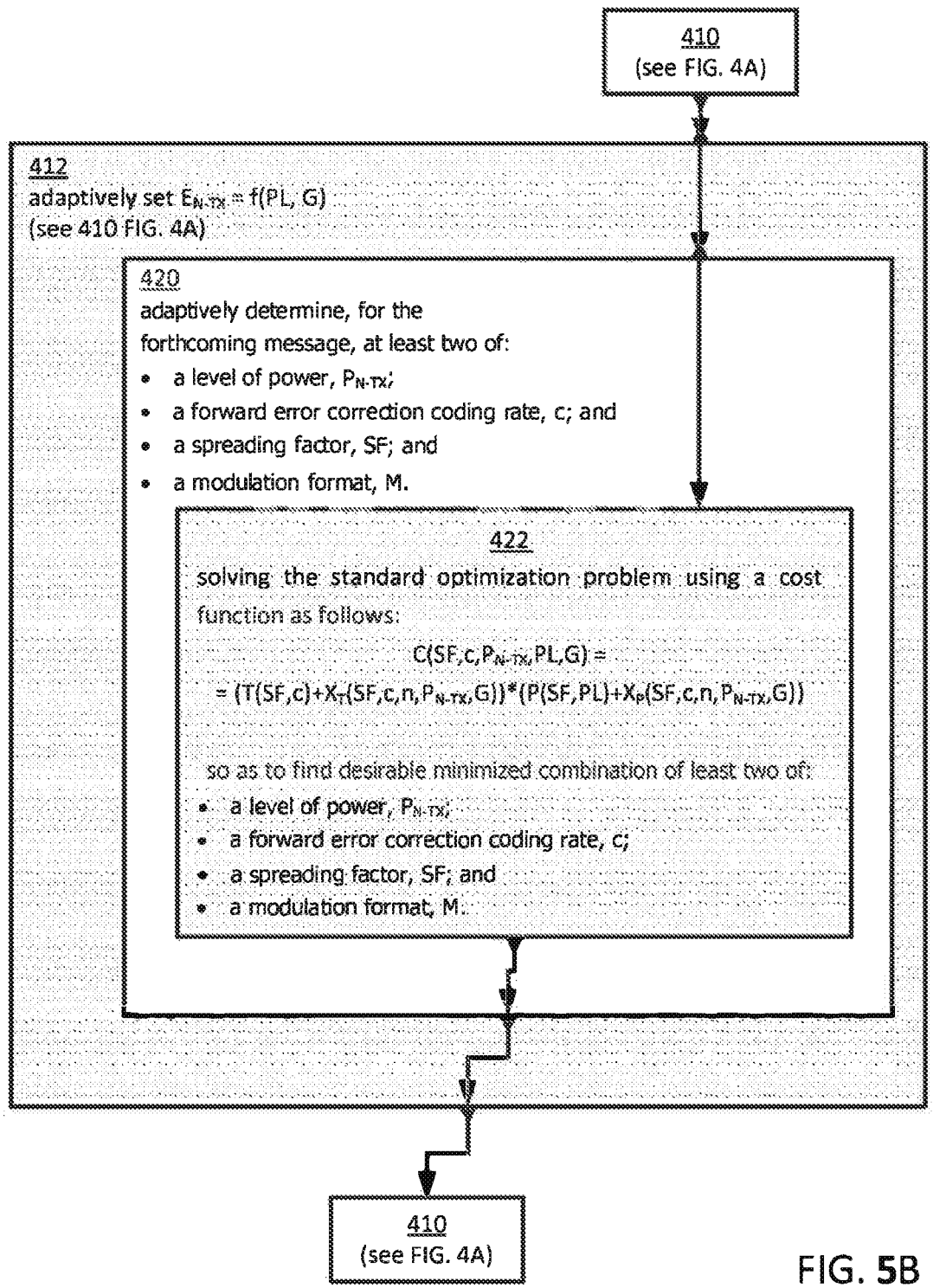

FIGS. 5A-5B are flowcharts illustrating a method of operating an instance of end node 102 to wirelessly communicate with central node 106, according to an embodiment of the present invention, with FIG. 5B illustrating one of the blocks of FIG. 5A in greater detail.

In FIG. 5A, there is a loop. As a general design consideration, no loop should be infinite, i.e., inescapable. Accordingly, flow in FIG. 5A starts at block 400 and proceeds to a decision block 402, where processor 108 decides if any exit criteria have been satisfied. If the outcome of decision block 402 is yes (one or more of the exit criteria are satisfied), then flow proceeds to block 403 and ends. If the outcome of decision block 402 is no (none of the exit criteria has been satisfied), then flow proceeds to a decision block 404.

At decision block 404, wireless IF 114" determines if a next instance 302 of the beacon signal has been received via wireless unit 114'. If the outcome of decision block 404 is no (the next instance of the beacon signal has NOT been received), then wireless IF 114" waits, e.g., then flow loops back to the input of decision block 402. If the outcome of decision block 404 is yes (the next instance of the beacon signal HAS been received), then flow proceeds to a block 406, where received-power sensor 130 measures a received power $P_{B-RX}$ of beacon signal. For example, the figure of merit EIRP (Effective Isotropic Radiated Power) can be used as $P_{B-RX}$. From block 406, flow proceeds to a block 408, where values stored in memory 110 are read. More particularly, from memory 110, a value of $P_{B-TX}$ (representing a presumed transmitted power of the beacon signal) is read by path-loss unit 132, and a value of G (representing a performance goal of end node 102) is read by transmit-energy unit 134. Alternatively, the value of G otherwise read at block 408 could be read after a block 410(discussed below) and before block 412 (discussed below). From block 408, flow proceeds to a block 410.

At block 410, path-loss unit 132 determines a path loss PL based on the received power $P_{B-RX}$ and the presumed transmitted power $P_{B-TX}$ of the beacon signal, i.e., $PL = f\{P_{B-RX}, P_{B-TX}\}$. For example, $PL = P_{B-RX} - P_{B-TX}$. From block 410, flow proceeds to a block 412, where transmit-energy unit 132 adaptively sets an energy level $E_{N-TX}$ (of a forthcoming message, to be transmitted via wireless IF 114" and wireless unit 114', based on PL and G.

Typically, an instance of end node 102 will be powered by a battery (not illustrated), e.g., a battery of small capacity such as a coin-type battery. As such, one factor in operating a given instance of end node 102 is the effect of a given energy level $E_{N-TX}$ of a forthcoming message on the life of its battery.

Not all instances of end node 102 will be located the same distance from central node 106 nor experience the same path loss there-between. As such, there are additional factors in operating a given instance of end node 102 that relate to path distance and path loss. More particularly, a factor in operating a given instance of end node 102 is the effect of a given energy level $E_{N-TX}$ of a forthcoming message on the transmission power and whether the power is sufficient to achieve a minimum desired probability that the forthcoming message will reach (be received by) central node 102.

Another factor in operating a given instance of end node 102 is the effect of a given energy level $E_{N-TX}$ of a forthcoming message in terms of the size of its spreading factor (or, in other words, the duration of its transmission time) and whether the forthcoming message that is assumed to be received by central node 102 will achieve suffer no more than a maximum acceptable degree of noise corruption (and so be understandable by central node 106). The transmission time is directly proportional to the spreading factor, and the noise corruption level in a received signal is inversely proportional to the spreading factor, the transmission time and the transmission power, respectively.

Accordingly, such factors and others can be taken into consideration by transmit-energy unit 132 in block 412. Block 412 is discussed in more detail below in the context of FIG. 5B. For each instance of the beacon signal (and thus for each instance of the frame as there is one frame per beacon signal), for example, transmit-energy unit 134 can determine one corresponding instance of the energy level $E_{N-TX}$ once; furthermore, transmit-energy unit 134 can send one or messages during a given frame, with each message during the frame being sent using the same the energy level $E_{N\text{-}TX}$. From block 412, flow proceeds from block 412 to a block 414.

At block 414, transmit-energy unit 134 sends, via wireless IF 114" and wireless unit 114', a message to central node 106 according to the energy level $E_{N\text{-}TX}$. From block 414, flow proceeds to loop back to decision block 402. An example of an exit criterion that could be determined in block 402 as being satisfied is a determination that flow has proceed to decision block 402 from block 414.

As noted above, FIG. 5B is a flowchart illustrating block 412 of FIG. 5A in more detail.

In FIG. 5B, block 412(the adaptive setting of an energy level $E_{N\text{-}TX}$ of a forthcoming message) is illustrated as including a block 420, in which transmit-energy unit 132 (and more particularly, standard optimizer 310) adaptively determines, for the forthcoming message, at least two of: a level of power, $P_{N\text{-}TX}$; a forward error correction coding rate, c; a spreading factor, SF, and a modulation rate, M. For example, M can be the LoRa™ modulation format, frequency shift keying ("FSK"), etc.

Changing each of $P_{N\text{-}TX}$, c, SF and M causes, as a consequence, the energy level $E_{N\text{-}TX}$ to change, and thus causes the energy consumed by the transmission to change. And changing two or more of $P_{N\text{-}TX}$, c, SF and M consequentially causes the energy level $E_{N\text{-}TX}$ to change. Hence, the energy level $E_{N\text{-}TX}$ is adaptively set by adaptively setting one or more of $P_{N\text{-}TX}$, c, SF and M, which results in adaptive transmission energy consumption.

Block 420 itself is illustrated as including a block 422, in which transmit-energy unit 132 (and more particularly, standard optimizer 310) solves a standard optimization problem. In general, a standard optimization problem is that of finding a best solution from all feasible solutions. Standard optimizer 310 is configured to use PL and G as inputs for finding a desirable minimized combination of the least two of $P_{N\text{-}TX}$, c, SF and M. Flow proceeds within block 412 to block 420, and then within block 420 to block 422. Likewise, flow proceeds outward from block 422 to block 420, and then outward from block 420 to block 412.

In other words, the outputs of blocks 420 and 422, respectively, can be one of several instances of a definition $DEF_{E_{N\text{-}TX}}$ of $E_{N\text{-}TX}$. Such instances of definition $DEF_{E_{N\text{-}TX}}$ include: a definition $DEF_{E_{N\text{-}TX}} \supset \{P_{N\text{-}TX}, c\}$; a definition $DEF_{E_{N\text{-}TX}} \supset \{P_{N\text{-}TX}, SF\}$; a definition $DEF_{E_{N\text{-}TX}} \supset \{P_{N\text{-}TX}, M\}$; a definition $DEF_{E_{N\text{-}TX}} \supset \{c, SF\}$; a definition $DEF_{E_{N\text{-}TX}} \supset \{c, M\}$; a definition $DEF_{E_{N\text{-}TX}} \supset \{SF, M\}$; a definition $DEF_{E_{N\text{-}TX}} \supset \{P_{N\text{-}TX}, c, SF\}$; a definition $DEF_{E_{N\text{-}TX}} \supset \{P_{N\text{-}TX}, c, M\}$; a definition $DEF_{E_{N\text{-}TX}} \supset \{P_{N\text{-}TX}, SF, M\}$; a definition $DEF_{E_{N\text{-}TX}} \supset \{c, SF, M\}$; and a definition $DEF_{E_{N\text{-}TX}} \supset \{P_{N\text{-}TX}, c, SF, M\}$;.

Values of the performance goal G include: values that maximize data-reliability of the data as received at the central node; values that optimize the energy level $E_{N\text{-}TX}$ relative to battery-chemistry-specific attributes of the battery sourcing the end node; e.g., relative to the battery-chemistry and physics of a coin cell battery; values that reflect a desired ratio of data-reliability versus battery management; and values that maximize network capacity (or, in other words, minimize time on air).

For example, transmit-energy unit 132 can be configured to solve the standard optimization problem using a cost function as follows:

$$C(SF,c,P_{N\text{-}TX},PL,G)=(T(SF,c)+X_T(SF,c,n,E_{N\text{-}TX},G))*(P(SF,PL)+X_P(SF,c,n,P_{N\text{-}TX},G))$$

wherein:
$P_{N\text{-}TX}$ is a target value of EIRP (Effective Isotropic Radiated Power) and is assumed to be a constant;
T(SF, c) is a time on air required to transmit the forthcoming message;
c is the forward error correction coding rate;
n denotes time dependence (discussed in more detail below); and
P(SF, PL) is a power consumed by the end node; and
$X_T(SF, c, n, P_{N\text{-}TX}, G)$ and $X_P(SF, c, n, P_{N\text{-}TX}, G)$ are a time-on-air weighting function and a total-transmission-power weighting function based SF, c, n, $P_{N\text{-}TX}$ and G, respectively; and wherein:
the evaluation of the cost function at PL and G is represented as follows:

$$\{SF, c, P_{N-TX}\}_{opt} = \operatorname*{argmin}_{SF,c,P_{N-TX}} C(SF, c, P_{N-TX}, PL, G)\bigg|_{G,PL}.$$

The weighting functions $X_T(SF, G)$ and $X_P(SF, G)$ can be determined empirically and/or heuristically. The weighting functions $X_T(SF, G)$ and $X_P(SF, G)$ can be read from memory 110 by standard optimizer 310.

For example, the time dependence, n, can be the number of re-transmissions of the same message. With each re-transmission, e.g., one of more of the factors SF, c, n, $P_{N\text{-}TX}$ and G can be increased, respectively. Alternatively, e.g., there can be a maximum number of re-transmissions permitted such that the factors SF, c, n, $P_{N\text{-}TX}$ and G can be maximized, respectively, with the last permitted re-transmission.

As a further example, transmit-energy unit 132 can be configured to relate the $X_T(SF, c, P_{N\text{-}TX}, G)$ and the $X_P(SF, c, P_{N\text{-}TX}, G)$ weighting functions as follows:
to maximize a life of a battery sourcing the end node, then set $X_T=0$ and $X_P=0$;
to minimize time on air, then set $X_T>0$ and $X_P=0$; and
to minimize peak current draw from the battery, then set $X_T=0$ and $X_P>0$; and
otherwise set $X_T>0$ and $X_P>0$.

Figure 6:
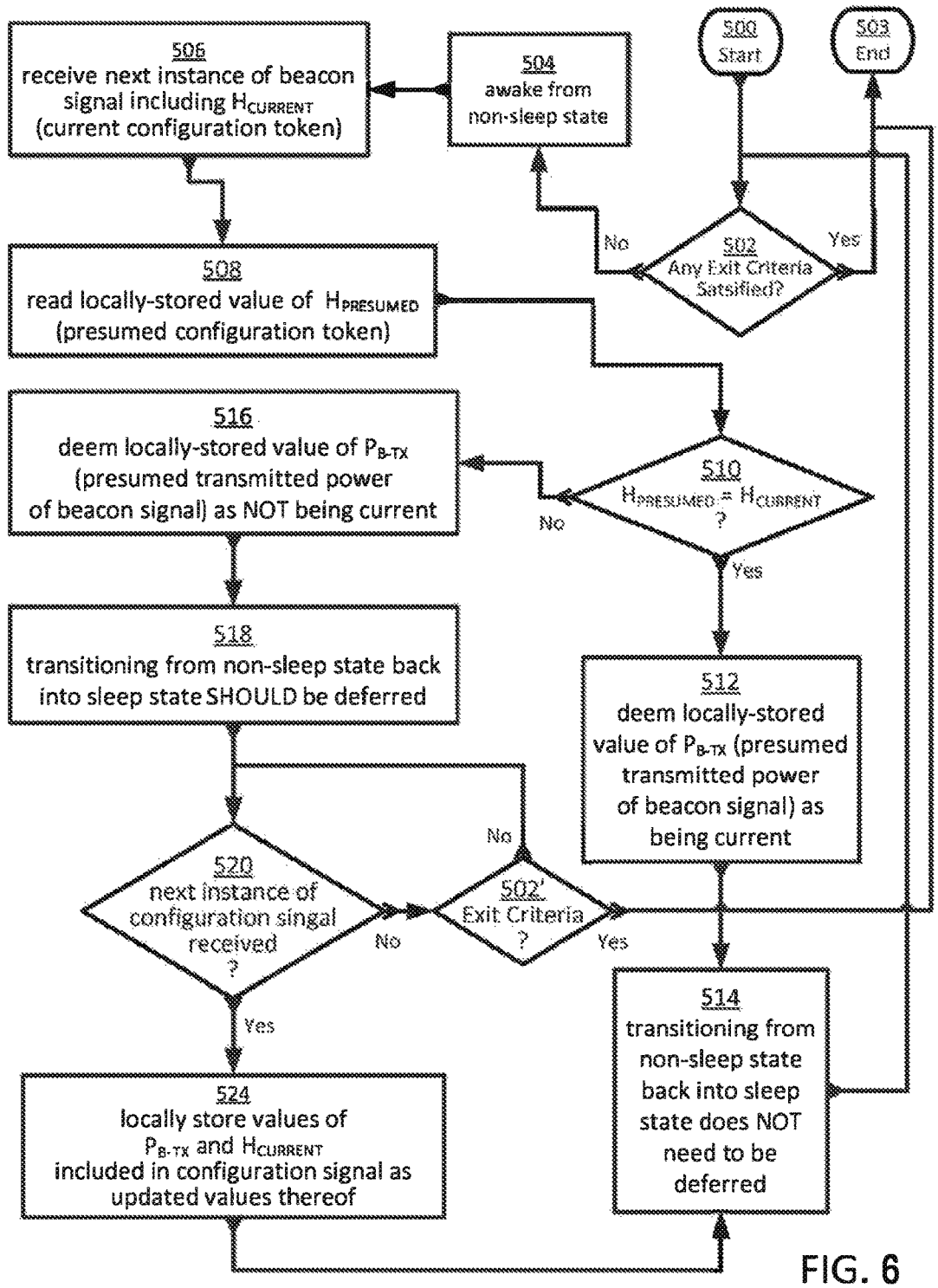
FIG. 6 is a flowchart illustrating another method of operating an instance of the end node, such as the collector, to wirelessly communicate with the central node, according to an embodiment of the present invention.

FIG. 6 is a flowchart illustrating another method of operating an instance of end node 102 to wirelessly communicate with central node 106, according to an embodiment of the present invention.

In FIG. 6, there is a loop. As a general design consideration, no loop should be infinite, i.e., inescapable. Accordingly, flow in FIG. 6 starts at block 500 and proceeds to a decision block 502, where processor 108 decides if any exit criteria have been satisfied. If the outcome of decision block 502 is yes (one or more of the exit criteria are satisfied), then flow proceeds to block 503 and ends. If the outcome of decision block 502 is no (none of the exit criteria has been satisfied), then flow proceeds to a block 504. At block 504, the instance of end node 102 awakes from a sleeping state. It is noted that instances of end node 102 each have operational states including: a non-sleep state; and a sleep state exhibiting reduced-power-consumption relative to the non-sleep state. The sleep state and/or the non-sleep state may itself/themselves be a set of states, respectively. From block 504, flow proceeds to a block 506.

At block 506, wireless IF 114" determines that a next instance 302 of the beacon signal has been received via wireless unit 114'. Each instance B of the beacon signal includes an instance H of a corresponding configuration token. Hence, upon receipt of the next instance B(i) of the beacon signal, wireless IF 114" thereby obtains the next (and then current) instance H(i) of the configuration token, and provides the same to transmit-energy unit 134.

The configuration token H is similar in some respects to a session token, as the latter is generally understood in computer science. A session token can be a unique identifier, e.g., in the form of a hash generated by a hash function, that is used to identify the current instance of a session. Here, the configuration token can be generated by configuration-signal generator 128 (as discussed below), e.g., in the form of a hash resulting from a hash function used by configuration-signal generator 128.

From block 506, flow proceeds to a block 508, where transmit-energy unit 134 reads a value $H_{PRESUMED}$ (representing a presumed configuration token) from memory 110. From block 508, flow proceeds to a decision block 510.

At decision block 510, transmit-energy unit 134 determines if the presumed configuration token $H_{PRESUMED}$ equals the current instance H(i) of the configuration token, if $H_{PRESUMED}$=H(i). If the outcome of decision block 510 is yes ($H_{PRESUMED}$=H(i)), then flow proceeds to a block 512, where transmit-energy unit 134 deems the status of PB-TX (again, representing a presumed transmitted power of the beacon signal that is stored in memory 110) as being current. From block 512, flow proceeds to a block 514, where transmit-energy unit 134 determines that transitioning from the non-sleep state back into the sleep state does NOT need to be deferred due to a non-current status of the presumed configuration token $H_{PRESUMED}$. Of course, there may be other reasons (not addressed herein) that warrant deferring the transition from the non-sleep state back into the sleep state. From block 514, flow proceeds to loop back to decision block 502. An example of an exit criterion that could be determined in block 502 as being satisfied is a determination that flow has proceed to decision block 502 from block 514.

If the outcome of decision block 510 is no ($H_{PRESUMED} \neq$ H(i)), then flow proceeds to a block 516, where transmit-energy unit 134 deems the status of the $P_{B-TX}$ (again, representing a presumed transmitted power of the beacon signal that is stored in memory 110) as NOT being current. From block 516, flow proceeds to a block 518, where transmit-energy unit 134 determines that transitioning from the non-sleep state back into the sleep state SHOULD be deferred due to the non-current status of the presumed configuration token $H_{PRESUMED}$. Of course, there may be additional reasons (not addressed herein) that warrant deferring the transition from the non-sleep state back into the sleep state. From block 518, flow proceeds to a decision block 520, with flow-control thereby being transferred from transmit-energy unit 134 to wireless IF 114".

At decision block 520, wireless IF 114" determines if a next instance 304 of the configuration signal has been received via wireless unit 114'. If the outcome of decision block 520 is no (the next instance of the configuration signal has NOT been received), then wireless IF 114" waits, e.g., then flow loops back to a decision block 502', where processor 116 decides if any exit criteria have been satisfied. If the outcome of decision block 502' is yes (one or more of the exit criteria are satisfied), then flow proceeds to block 503 and ends. If the outcome of decision block 502' is no (none of the exit criteria has been satisfied), then flow proceeds back to the input of decision block 520. If the outcome of decision block 520 is yes (the next instance of the configuration signal HAS been received), then flow proceeds to a block 524.

Each instance of the configuration signal includes an instance of $P_{B-TX}$ (again, representing transmitted power of the beacon signal as measured by transmitted-power sensor 126 of central node 106) and an instance H of a corresponding configuration token. Hence, upon receipt of the next instance of the configuration token, wireless IF 114" thereby obtains the next (and then current) instance of $P_{B-TX}$ and the next (and then current) instance H(i) of the configuration token.

At block 524, wireless IF 114" stores the next (and then current) instance of $P_{B-TX}$ and the next (and then current) instance H(i) of the configuration token in memory 110 as the presumed transmitted power $P_{B-TX}$ and the presumed configuration token $H_{PRESUMED}$, respectively. From block 524, flow proceeds to block 514 (discussed above).

Figure 7:
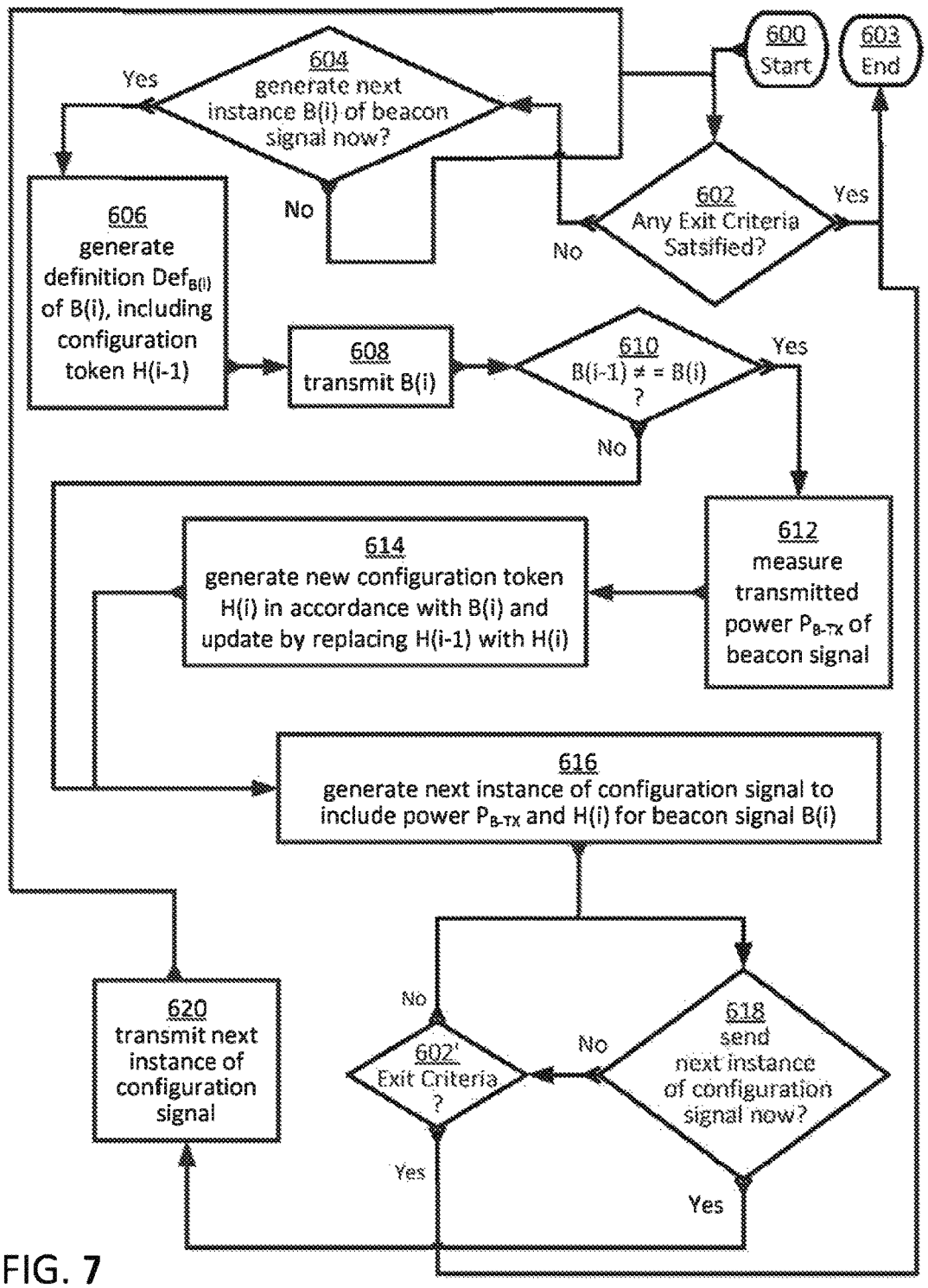
FIG. 7 is a flowchart illustrating a method of operating the central node to wirelessly communicate with instances of the end node, such as the collector, according to an embodiment of the present invention.

FIG. 7 is a flowchart illustrating a method of operating central node 106 to wirelessly communicate with instances of end node 102, according to an embodiment of the present invention.

In FIG. 7, there is a loop. As a general design consideration, no loop should be infinite, i.e., inescapable. Accordingly, flow in FIG. 7 starts at block 600 and proceeds to a decision block 602, where processor 116 decides if any exit criteria have been satisfied. If the outcome of decision block 602 is yes (one or more of the exit criteria are satisfied), then flow proceeds to block 503 and ends. If the outcome of decision block 602 is no (none of the exit criteria has been satisfied), then flow proceeds to a decision block 604.

At block 604, beacon-signal generator 124 determines if enough time has elapsed as a condition of generating the next instance B(i) of the beacon signal. It is to be recalled that central node 106, and more particularly beacon-signal generator 124, is configured to periodically transmit (via wireless IF 122" and wireless unit 122') the beacon signal B at an interval, $I_{BEACON}$. If the outcome of decision block 604 is no (enough time has NOT elapsed), then beacon-signal generator 124 waits, e.g., then flow loops back to the input of decision block 402. If the outcome of decision block 604 is yes (enough time HAS elapsed), then flow proceeds to a block 606.

At block 606, beacon-signal generator 124 generates a next definition $Def_{B(i)I}$ of the next beacon signal B(i) that includes a previous value H(i−1) of the configuration token, $Def_{B(i)I} \supset$ H(i−1). From block 606, flow proceeds to a block 608, where beacon-signal generator 124 (via wireless IF 114" and wireless unit 114') sends beacon signal B(i) to the instances of end node 102. From block 608, flow proceeds to a decision block 610.

At decision block 610, transmitted-power sensor 126 determines if the $i^{th}$ and $(i-1)^{th}$ instances of the beacon signal B differ such that B(i−1)≠B(i). If the outcome of decision block 610 is no (B(i−1)=B(i)), then flow proceeds to a block 616(discussed below). If the outcome of decision block 610 is yes (B(i−1)≠B(i)), then flow proceeds to a block 612, where transmitted-power sensor 126 measures a transmitted power, $P_{B-TX}$, of B(i). For example, the figure of merit EIRP (Effective Isotropic Radiated Power) can be used as $P_{B-TX}$. From block 612, flow proceeds to a block 614, where configuration-signal generator 128 is configured to generate a new configuration token H(i) in accordance with B(i) and updates memory 110 by replacing H(i−1) with H(i). From block 614, flow proceeds to a block 616 (discussed below).

At block 616, configuration-signal generator 128 generates a new configuration signal that includes H(i) and a value representing a transmitted power, $P_{B-TX}$, of B(i), $Def_{config-signal} \supset$ H(i), $P_{B-TX}$. From block 616, flow proceeds to a decision block 618, where configuration-signal generator 128 determines if enough time has elapsed as a condition of sending the next instance of the configuration signal. It is to be recalled that central node 106, and more particularly configuration-signal generator 128, is configured to periodically transmit the configuration signal at an interval, $I_{CONFIG}$. If the outcome of decision block 604 is no (enough time has NOT elapsed), then configuration-signal generator 128 waits, e.g., then flow proceeds to a decision block 602', where processor 116 decides if any exit criteria have been satisfied. If the outcome of decision block 602' is yes (one or more of the exit criteria are satisfied), then flow proceeds to block 603 and ends. If the outcome of decision block 602' is no (none of the exit criteria has been satisfied), then flow proceeds back to the input of decision block 618.

If the outcome of decision block 618 is yes (enough time HAS elapsed), then flow proceeds to a block 620. At block 620, configuration-signal generator 128 (via wireless IF 114" and wireless unit 114') sends the next instance of the configuration signal. From block 620, flow loops back to decision block 602 (discussed above).

As noted, the value of G (representing a performance goal of end node 102) and the weighting functions $X_T(SF, G)$ and $X_T(SF, G)$ can be read from memory 110, respectively. As part of an initial configuration of an instance of end node 102, the value of G and the weighting functions $X_T(SF, G)$ and $X_T(SF, G)$ can be stored in memory 110. Optionally, the value of G, the weighting function $X_T(SF, G)$ and the weighting function $X_T(SF, G)$ can be updated, e.g., an additional pieces of information included in an instance of configuration signal 304, respectively. For example, in cooperation with processor 108), wireless IF 114" can extract an updated value of G, the updated weighting function $X_T(SF, G)$ and/or the updated weighting function $X_T(SF, G)$ from an instance of configuration signal 304, and then store the respective updates, e.g., by overwriting their corresponding predecessors, respectively.

Figure 8:
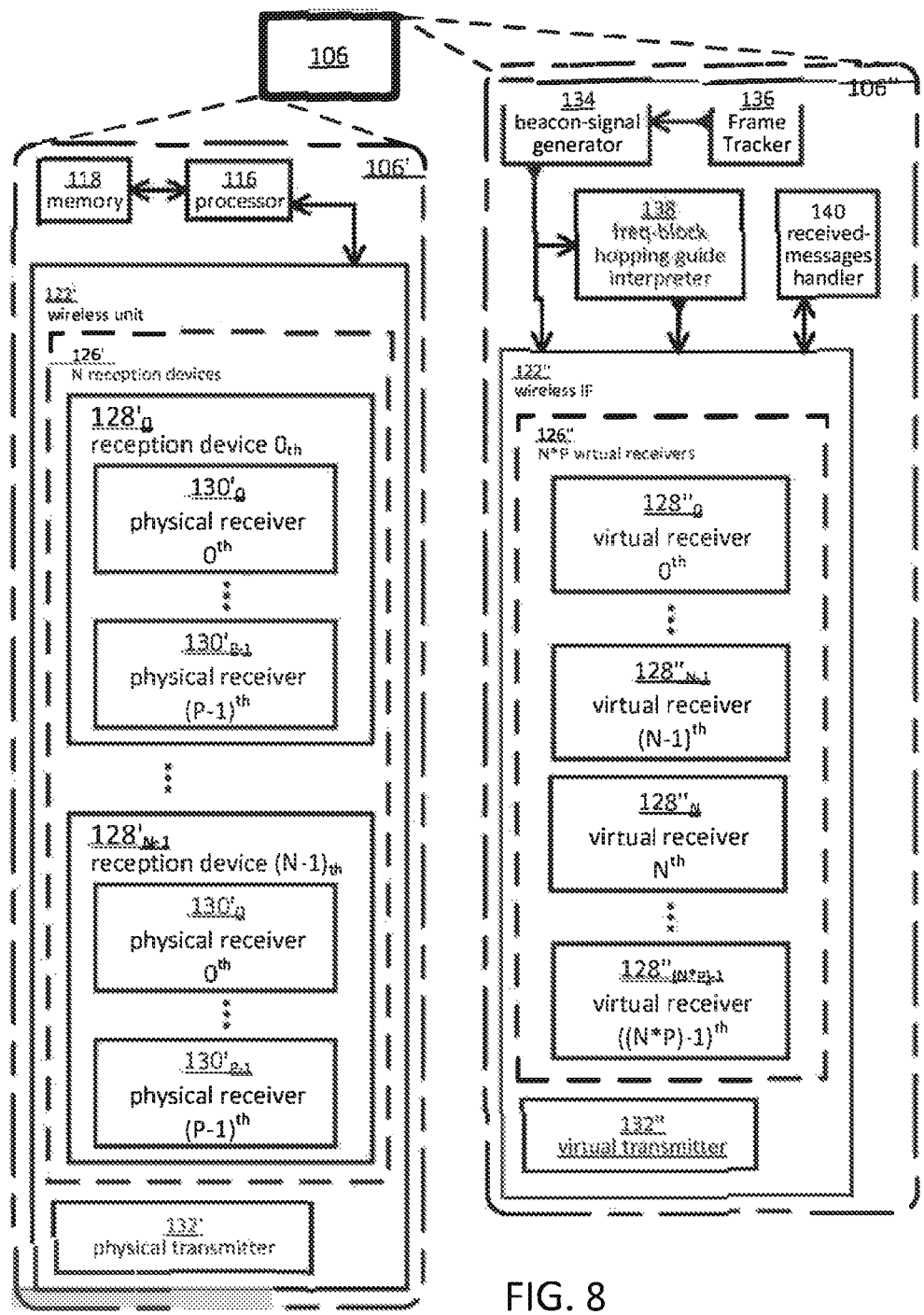
FIG. 8 is a block diagram illustrating the physical units and the functional units of a central node (e.g., the central node of FIG. 2) in more detail, according to an embodiment of the present invention.

FIG. 8 is a block diagram illustrating the physical units and the functional units of another embodiment of central node 106 in more detail.

In FIG. 8, in terms of the physical components (as illustrated by exploded view 106') included in each instance of central node 106, namely the one or more instances of a processor 116, memory 118 and a wireless unit 122', it is wireless unit 122' which is illustrated in more detail relative to FIG. 8.

More particularly, FIG. 8 illustrates wireless interface 122' as including: a group 126' of N reception banks 128'$_0$-128'$_{N-1}$, where N is an integer, and $2 \leq N$. Each of the N reception banks 128'$_0$-128'$_{N-1}$ in group 126' can include P physical receivers 130'$_0$-130'$_{P-1}$, where P is a positive integer, $2 \leq P$. For example, N=2 and P=4. Each of the P physical receivers 130'$_0$-130'$_{P-1}$ can be tuned to any of the channels, CHs, e.g., available for uplink (that is, transmission in the direction from an instance of end node 102 to central node 106) in the given unlicensed spectrum. Recalling the assumption that, at maximum, there are Q channels which potentially can be used for transmissions (uplink direction) from instances of end node 102 to central node 106, it is noted that N*P<Q, i.e., that there are fewer receivers in central node 102 than there are channels which potentially can be used for uplink transmissions.

For example, each of the N reception banks 128'$_0$-128'$_{N-1}$ being implemented by a Model SX1257 FR Front-End Transceiver commercially available from SEMTECH Corp. Also, for example, central node 106 can be a LoRa/SYMPHONY Gateway having, e.g., 8 channels (such as Model No. LL-BST-8 commercially available from LINK LABS, LLC). Wireless unit 122' further includes at least one physical transmitter 132', e.g., corresponding to one of the transmitters in one of the Model SX1257 FR Front-End Transceivers. Here, an alternate term for channel CH is intermediate frequency, IF.

In FIG. 8, in terms of the functional components (as illustrated by exploded view 106"), each instance of central node 106 includes: a group 126" of N*P virtual receivers 128"$_0$, . . . , 128"$_{N-1}$, 128"$_N$, . . . , 128"$_{N*P-1}$, where P is a positive integer, and $2 \leq P$; a virtual transmitter 132'; a beacon signal generator 134; a frame tracker 136; a frequency-block hopping guide interpreter 138; and a received-messages handler 140.

Briefly, in operation, an instance of end node 102 can transmit messages to central node 106 as follows. Wireless unit 114' can be configured to receive (downlink direction) and transmit (uplink direction) messages. An instance of end node 102 (via wireless unit 114' and wireless interface 114") can receive (downlink direction), from central node 106, an instance of a non-hopping beacon signal, B, periodically-transmitted (e.g., at an interval of 2 sec or 0.5 Hz) from central node 106 (via wireless unit 122' and wireless interface 122"). Each instance B(i) of the beacon signal can include: a frame number, FN(i), of a frame corresponding thereto; and identification, IDCN, of central node 106. The IDCN does not necessarily need to be a unique identifier such as a GUID (Globally Unique Identifier)/UUID (Universally Unique Identifier). Rather, the IDCN should at least be unique among geographically neighboring (or co-located) instances of central node 106. For example, IDCN can be one of 16 different numbers.

Frequency-block hopping guide interpreter 138 can be configured to interpret a frequency-block hopping guide according to FN(i) and IDCN thereby to determine a corresponding set, CSET(i), of at least two channels available to the instance of end node 102 for transmission thereover (uplink direction), respectively, during frame FN(i). It is to be recalled: (A) that, at maximum, there is assumed to be Q channels which potentially can be used for transmissions (uplink direction) from instances of the end node 102 to central node 106; and (B) that central node is provided with N*P physical receivers, where N*P<Q.

With central node 106 having N*P<Q physical receivers, at least some hopping-synchronization is employed such that it would be inaccurate to describe the associated hopping-synchronization scheme as a zero synchronization scheme. Conversely, because central node 106 does not know on which (if any) of the N*P channels in CSET(i) there might be transmissions forthcoming from one of more of the instances of end node 102 during frame FN(i), consequently central node 106 must tune its N*P physical receivers to listen on all of the N*P channels in CSET(i), respectively. Hence, it would be inaccurate to describe the associated hopping-synchronization scheme as a complete synchronization scheme. Accordingly, the associated hopping-synchronization scheme can be described as a partial hopping-synchronization scheme.

The frequency-block hopping guide (also discussed in more detail below) establishes: a total of L frames; a set of channels CSET for each frame, respectively; and that, for any two consecutive ones of the L frames, FN(j) and FN(j+1), the corresponding sets CSET(j) and CSET(j+1) will be different, CSET(j)≠CSET(j+1). Channel selector 142 is configured to select, at least pseudo-randomly (albeit using a different pseudo random number generator than frequency-block hopping guide interpreter 138), at least one channel amongst the set CSET(i). Message generator 144 can be configured to generate at least one message using the at least one selected channel, respectively. Wireless interface 114" (via wireless unit 114') can be configured, among other things, to wirelessly transmit (uplink direction) the at least one message, respectively. It is noted that i and j are non-negative integers, L is an integer, and 2≤L, e.g., L=256.

Conversely (and, again, briefly), in operation, central node 106 can transmit (downlink direction) a beacon signal, B, to instances of end node 102, and then listen (uplink direction) for messages from the instances of end node 102, respectively, as follows. Frame tracker 136 can be configured to determine a frame number, FN(i). Beacon signal generator 134 can be configured to receive the frame number FN(i) and generate periodically an instance, B(i), of a non-hopping beacon signal B(i) which includes: the frame number, FN(i); and the identification, IDCN, of central node 106. For example, though the beacon signal is transmitted in an unlicensed spectrum, each instance B(i) of the beacon signal can be of sufficient bandwidth that it does not have to hop, i.e., it can be a non-hopping signal and yet be can be transmitted permissibly in the unlicensed spectrum because it is of sufficient bandwidth.

Wireless unit 122' can be configured to receive (uplink direction) and transmit (downlink direction) messages. Wireless interface 122" can be configured to transmit (downlink direction, via wireless unit 122') the instance B(i) of the beacon signal to the instances of end node 102, thereby starting an elapse of time corresponding to frame FN(i). As with the instances of end node 102, frequency-block hopping guide interpreter 138 can be configured to interpret a frequency-block hopping guide according to FN(i) and IDCN thereby to determine a corresponding set, CSET(i), of at least two channels available to the instance of end node 102 for transmission thereover, respectively, during frame FN(i). Also, as with the instances of end node 102, the frequency-block hopping guide (also discussed in more detail below) establishes: a total of L frames; a set of channels CSET for each frame, respectively; and that, for any two consecutive ones of the L frames, FN(j) and FN(j+1), the corresponding sets CSET(j) and CSET(j+1) will be different, CSET(j)≠CSET(j+1).

Wireless interface 122" can be further configured to listen (uplink direction, via group 126" that includes N*P virtual receivers $128"_0, \ldots, 128"_{N-1}, 128"_N, \ldots, 128"_{N*P-1}$, where P is a positive integer, 2≤P, e.g., N=2 and P=4), during frame FN(i), on each of the at least two channels in the set CSET(i) for one or more transmissions (uplink direction) from instances of end nodes 102, respectively. Again, it is noted that i and j are non-negative integers, L is an integer, and 2≤L, e.g., L=256.

Each of central node 106 and the instances of end node 102 includes the same instance of frequency-block hopping guide interpreter 138. For example, at the time of manufacture, the same instance of frequency-block hopping specification 402 can be stored in memories 118 and 110 (e.g., non-volatile memories 120A and 112A) of central node 106 and the instances of end node 102, respectively. Upon initialization, the instances of frequency-block hopping guide interpreter 138 in central node 106 and the instances of end node 102, respectively, can generate corresponding instances of frequency-block hopping maps and/or frequency-block hopping schedules, respectively.

If central node 106 and the instances of end node 102 are synchronized, then manipulation of the same instance of frequency-block hopping specification 402 by processors 116 and 108 can generate the same corresponding instances of frequency-block hopping maps and/or frequency-block hopping schedules, respectively. Such synchronization can be provided, e.g., by the instances B(i) of the beacon signal that are transmitted periodically from central node 106 using the same channel/IF (again, the beacon signal is non-hopping), in particular by the instances FN(i) of the frame number included in the payloads of the instances B(i) of the beacon signal, respectively. Accordingly, when instances of frequency-block hopping guide interpreter 138 in central node 106 and the instances of end node 102 access their respective instances, e.g., of the frequency-block hopping schedules based on frame FN(i), such instances of frequency-block hopping guide interpreter 138 each will determine the same set CSET(i) of channels available for transmission thereover by the instances of end node 102 during frame FN(i).

Such synchronized generation of instances of frequency-block hopping maps and/or frequency-block hopping schedules includes the generation of pseudo-random numbers (see discussion of pseudo code example, below). Each of central node 106 and the instances of end node 102 includes the same instance of pseudo random number generator, e.g., a linear congruential generator, LCG. As a practical matter, the LCG is sufficiently deterministic that the resulting instances of frequency-block hopping maps and/or frequency-block hopping schedules will be the same, respectively. And yet the LCG is sufficiently pseudo random with respect to the numbers it generates that the resulting instances of frequency-block hopping maps and/or frequency-block hopping schedules will satisfy the hopping requirements, etc., promulgated for the given unlicensed spectrum by a government's regulatory authority.

So long as a given instance of end node 102 is connected to the same/first instance of central node 106, then its instances of frequency-block hopping map and/or frequency-block hopping schedule remain valid. If, however, the given instance of end node 102 that had been connected to the same/first instance of central node 106 becomes connected to a different/second instance of central node 106, then the given instance of end node 102 would need to regenerate its instances of frequency-block hopping map and/or frequency-block hopping schedule according to the corresponding identification IDCN of the different instance of central node 106.

Figure 9:
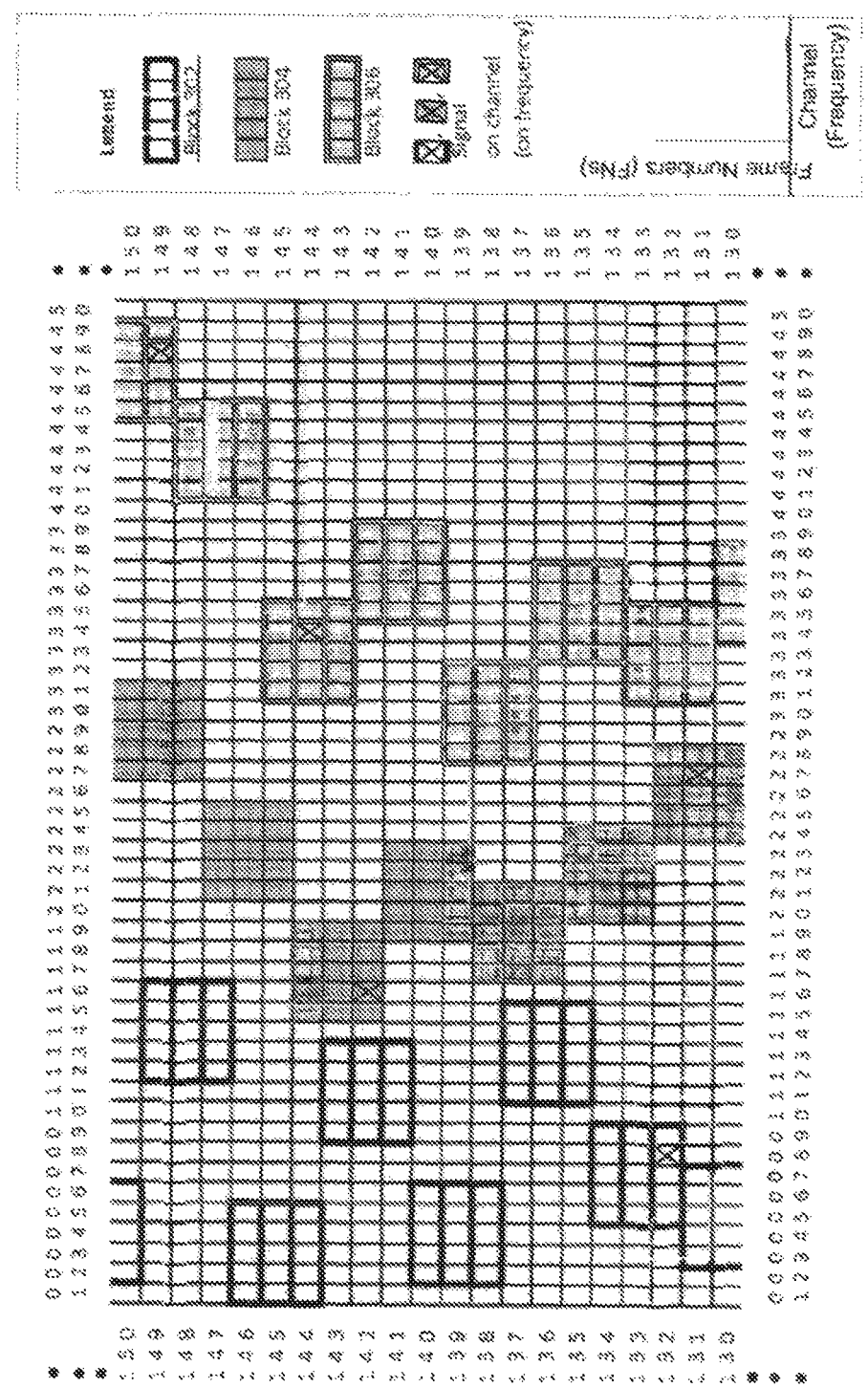
FIG. 9 is a two-dimensional plot illustrating an example of how blocks of contiguous frequencies hop from one frame to the next based on a frequency-block hopping guide, according to an embodiment of the present invention.

FIG. 9 is a two-dimensional plot illustrating an example of how blocks 302-306 of contiguous frequencies hop from one frame to the next based on a frequency-block hopping guide, according to an embodiment of the present invention.

In the example of FIG. 9, the X-axis represents uplink channels (to which contiguous intermediate frequencies ("IFs") correspond, respectively) while the Y-axis represents frame numbers. For simplicity, it has been assumed in FIG. 3 that there are only 50 uplink channels, i.e., Q=50. Again, this is merely an example as other values of Q are contemplated. Also for simplicity, only frames 130-150 have been illustrated in FIG. 3.

Also in the example of FIG. 9, it has been assumed that there are N=3 reception banks $128'_0$-$128'_2$ in group 126', with each of reception banks $128'_0$-$128'_2$ including P=5 physical receivers $130'_0$-$130'_4$, thereby providing a corresponding 15=3*5=N*P virtual receivers $128"_0, \ldots, 128"_{14}$ in group 126". Again, this is merely an example as other values for N and P are contemplated.

In frame 130, block 302 includes channels 03-07, block 304 includes channels 24-28 and block 306 includes channels 34-38 such that a channel set CSET(130) is {03-07,24-28,34-38}. It is noted that set CSET(130) represents the channels available to an instance of end node 102 for transmission thereover during frame FN(130), respectively.

In the next frame, namely frame 131, block 302 still includes channels 03-07 and block 304 still includes channels 24-28, but block 306 now includes channels 31-35 such that a channel set CSET(131) is {03-07,24-28,31-35}. It is noted that set CSET(130) represents the channels available to an instance of end node 102 for transmission thereover during frame FN(131), respectively. From frame 130 to frame 131, one block hops, namely block 306.

In frame 132, block 304 still includes channels 24-28 and block 306 still includes channels 31-35, but now block 302 includes channels 05-09 such that a channel set CSET(132) is {05-09,24-28,31-35}. From frame 131 to frame 132, one block hops, namely block 302. In frame 133, block 302 still includes channels 05-09 and block 306 still includes channels 31-35, but now block 304 includes channels 20-24 such that a channel set CSET(133) is {05-09,20-24,31-35}. From frame 132 to frame 133, one block hops, namely block 304. In frame 134, block 302 still includes channels 05-09 and block 304 still includes channels 20-24, but now block 306 includes channels 33-37 such that a channel set CSET(134) is {05-09,20-24,33-37}. From frame 133 to frame 134, one block hops, namely block 306.

In FIG. 9, for any two consecutive ones of the frames, FN(j) and FN(j+1), channels comprising only one of the N=3 blocks, namely block $BK_H$, change between the corresponding sets CSET(j) and CSET(j+1) such that $BK_H(j) \neq BK_H(j+1)$. In other words, relative to frame 130 and set CSET(130), the hopping block $BK_H(131)$ for frame 131 and set CSET(131) is block 306. Relative to frame 131 and set CSET(131), the hopping block $BK_H(131)$ for frame 132 and set CSET(132) is block 302; relative to frame 132 and set CSET(132), the hopping block $BK_H(133)$ for frame 133 and set CSET(133) is block 304; relative to frame 133 and set CSET(133), the hopping block $BK_H(134)$ for frame 134 and set CSET(134) is block 306; etc.

Also in FIG. 9, it should be observed that each of blocks 302-306 stays the same for three frames and then changes on the fourth frame. In particular, in the range of frames 132-149, block 302 stays the same for frames 132-134, for frames 135-137, for frames 138-140, for frames 141-143, for frames 144-146 and for frames 147-149. In the range of frames 130-150, block 304 stays the same for frames 130-132, for frames 133-135, for frames 136-138, for frames 139-141, for frames 142-144, for frames 145-147 and for frames 148-150. In the range of frames 131-148, block 306 stays the same for frames 131-133, for frames 134-136, for frames 137-139, for frames 140-142, for frames 143-145 and for frames 146-148.

Though central node 106 listens on all of the available channels in a given set CSET(j) during a given frame FN(j), one or more messages are not necessarily transmitted from instances of end node 102 during FN(j). It should also be observed in FIG. 9 that most of the channels available during a given frame FN(j) go unused, i.e., do not experience a message being transmitted thereover from an instance of end node 102 to central node 106 while the latter listens. In FIG. 9, a message transmitted from an instance of end node 102 is indicated by an "X" appearing in a given channel for a given frame, namely {FN(j),CH(k)}. For example, it is assumed in FIG. 3 that messages are transmitted from an instances of end node 102 in {FN(j),CH(k)}={131,27}, {FN(j),CH(k)}={132,08}, {FN(j),CH(k)}={142,16}, {FN(j),CH(k)}={144,34} and {FN(j),CH(k)}={149,48}. By contrast, in frames FN(130), FN(133)-FN(141), FN(143), FN(145)-FN(148) and FN(150), no messages are transmitted from an instance of end node 102 to central node 106.

Figure 10:
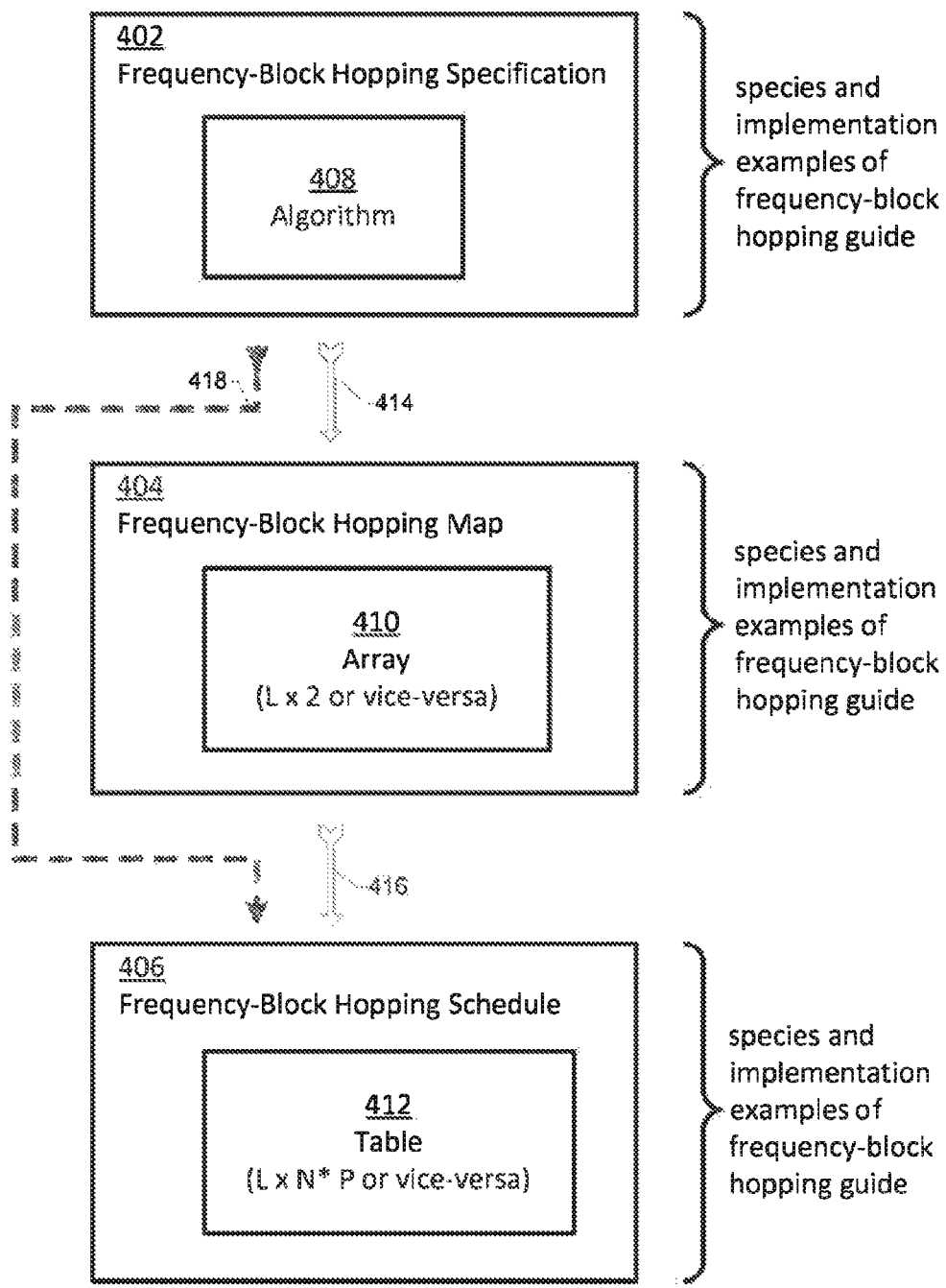
FIG. 10 is a block diagram illustrating species and implementation examples of a frequency-block hopping guide, plus derivational flow there-between, respectively, according to an embodiment of the present invention.

FIG. 10 is a block diagram illustrating species examples and implementation examples of a frequency-block hopping guide, plus derivational flow there-between, respectively, according to an embodiment of the present invention.

In FIG. 10, a first example species of a frequency-block hopping guide is a frequency-block hopping specification 402, of which an implementation example is an algorithm 408, e.g., in particular, pseudo code (discussed below). A second example species of a frequency-block hopping guide is a frequency-block hopping map 404, of which an implementation example is an array 410, e.g., in particular, an L×2 or 2×L array (discussed below). A third example species of a frequency-block hopping guide is a frequency-block hopping schedule 406, of which an implementation example is a table 412, e.g., in particular, a table having L rows and N*P columns or vice-versa (N*P rows and L columns) (discussed below). Again, these are merely examples as other species and implementation examples, respectively, are contemplated.

Frequency-block hopping map 404 can be derived from frequency-block hopping specification 402, as indicated by arrow 414 (and as discussed below). Frequency-block hopping schedule 406 can be derived from frequency-block hopping map 404, as indicated by arrow 416 (and as discussed below). In other words, frequency-block hopping schedule 406 can be derived indirectly from frequency-block hopping specification 402. Alternatively, frequency-block hopping schedule 406 can be derived directly from frequency-block hopping specification 402, as indicated by dashed arrow 418.

FIG. 11A is a particular implementation example of frequency-block hopping map 404 (which itself is a species of a frequency-block hopping guide), according to an embodiment of the present invention.

For FIG. 11A, the particular implementation example of frequency-block hopping map 404 is an L×2 array (data structure) for which it is assumed that L=256. Again, this is merely an example as other values for L are contemplated. The hopping pattern prescribed by hopping map 404 in FIG. 5A is cyclical. Upon reaching frame FN(L−1), the next frame is understood to be FN(0); for L=256, upon reaching FN(255), the next frame is FN(0).

It is noted that FIG. 11A also assumes: there are N=2 reception banks $128'_0$-$128'_1$ in group 126', with each of reception banks $128'_0$-$128'_1$ including P=4 physical receivers $130'_0$-$130'_3$, thereby providing a corresponding 8=2*4=N*P virtual receivers $128''_0, \ldots, 128''_7$ in group 126''; each block of P=4 contiguous channels can be determined by designation of a root channel, $CH_R$, which in FIG. 11A is assumed to be the channel of lowest frequency in the block thereby determining a given block as $\{CH_R+0;CH_R+1;CH_R+2;CH_R+3\}$; there are 152 possible channels {0, . . . , 151} in the unlicensed spectrum of interest, of which 148=152−4 are root channel $CH_R$ candidates, with the maximum value of any channel being 151 and the maximum value of the root channel $CH_R$=148 else, e.g., if $CH_R$=149, then $\{CH_R+0;CH_R+1;CH_R+2;CH_R+3\}=\{149,150,151,152\}$, i.e., $CH_R+3$ would take on an illegal value of 152. Again, this is merely an example as other values for N and P are contemplated.

Illustrated in FIG. 11A is a particular implementation example of a frequency-block hopping map 404, namely an L×2 array, L=256. As noted above in the discussion above of FIG. 10, frequency-block hopping map 404 itself is a second example species of a frequency-block hopping guide.

For simplicity, the array in FIG. 11A has been illustrated as eight instances of a 33×2 table (including the header row), with the first instance of the table corresponding to frame numbers FN(000) to FN(031), the second instance of the table corresponding to frame numbers FN(032) to FN(063), etc. In each of the tables in FIG. 11A, the left column represents the frame number FN(i) and the right column represents the root channel, $CH_R$, for the corresponding hopping block $BK_H$. Again, an alternate term for channel CH is intermediate frequency, IF, such that root channel $CH_R$ is equivalent to root IF, $IF_R$.

Again, each frame FN(j) has a corresponding set CSET(j) of channels available during frame FN(i) for transmission thereover (uplink) by instances of end node 102. For any two consecutive ones of the frames, FN(j) and FN(j+1), channels comprising only one of the N blocks (N=2 in FIG. 5A), namely block $BK_H$, change between the corresponding sets CSET(j) and CSET(j+1) such that $BK_H(j) \neq BK_H(j+1)$.

According to the example values in the particular implementation of frequency-block hopping map 404 illustrated in FIG. 11A, for map entry 035, map(035)=64 such that for frame FN(035), $CH_R$=64; for map entry 074, map(074)=49 such that for frame FN(074), $CH_R$=49; for map entry 175, map(175)=110 such that for frame FN(175), $CH_R$=110; for map entry 219, map(219)=110 such that for frame FN(219), $CH_R$=112; etc.

Figure 11B:
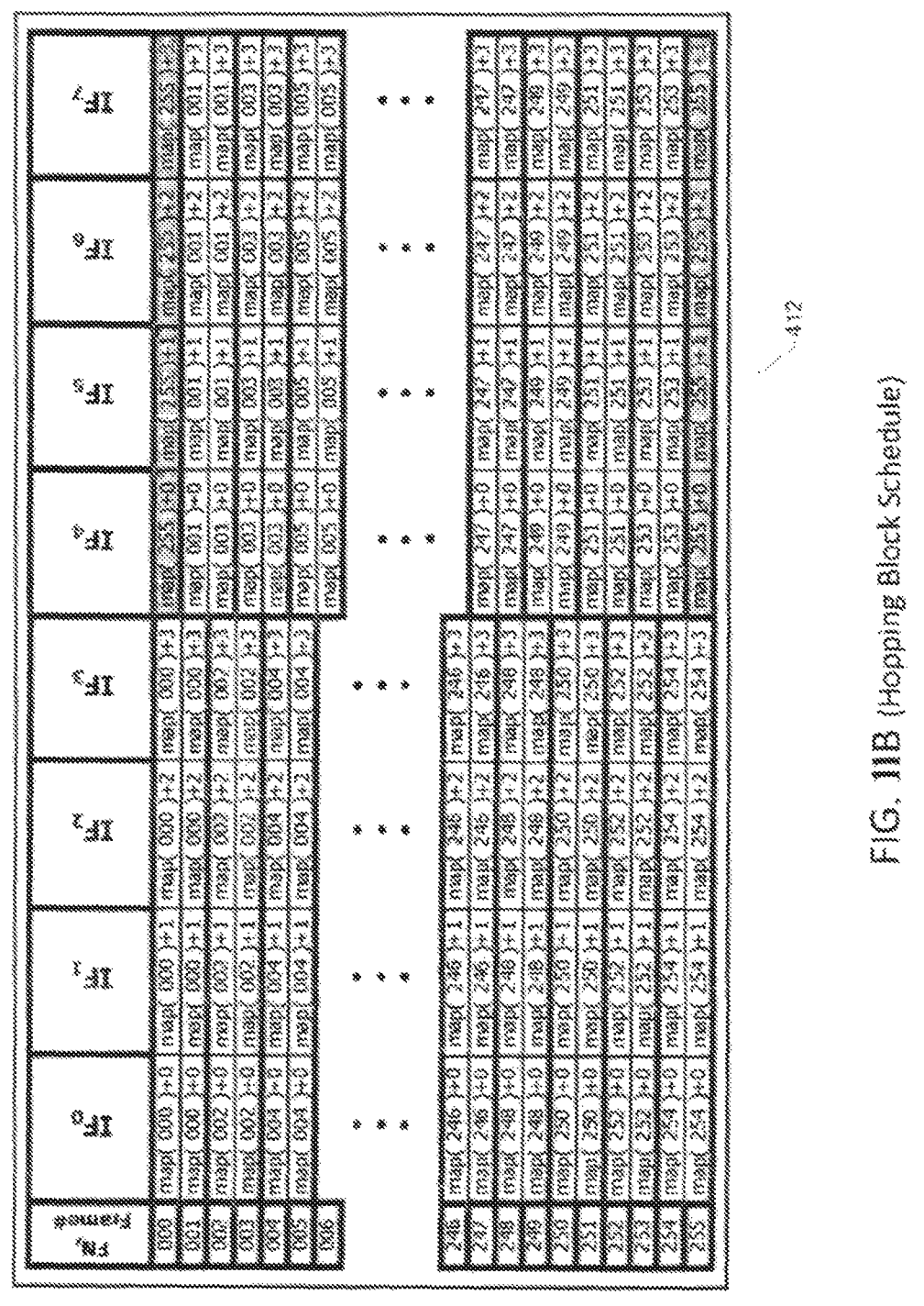

FIG. 11B is a particular implementation example of frequency-block hopping schedule 406 (which itself is a species of a frequency-block hopping guide), according to an embodiment of the present invention.

For FIG. 11B, the particular implementation example of frequency-block hopping schedule 406 is (L+1)×(N*P+1) table (data structure) for which it is assumed that L=256. Again, this is merely an example as other values for L are contemplated. The hopping pattern prescribed by hopping schedule 406 in FIG. 5B is cyclical. Upon reaching frame FN(L−1), the next frame is understood to be FN(0); for L=256, upon reaching FN(255), the next frame is FN(0).

It is noted that FIG. 11B (like FIG. 11A) also assumes: there are N=2 reception banks $128'_0$-$128'_1$ in group 126', with each of reception banks $128'_0$-$128'_1$ including P=4 physical receivers $130'_0$-$130'_3$, thereby providing a corresponding 8=2*4=N*P virtual receivers $128''_0, \ldots, 128''_7$ in group 126"; each block of P=4 contiguous channels can be determined by designation of a root channel, $CH_R$, which in FIG. 5B is assumed to be the channel of lowest frequency in the block thereby determining a given block as $\{CH_R+0; CH_R+1; CH_R+2; CH_R+3\}$; there are Q=152 possible channels $\{0, \ldots, 151\}$ in the unlicensed spectrum of interest, of which 148=152-4 are root channel $CH_R$ candidates, with the maximum value of any channel being 151 and the maximum value of the root channel $CH_R$=148 else, e.g., if $CH_R$=149, then $\{CH_R+0;CH_R+1;CH_R+2;CH_R+3\}=\{149,150,151,152\}$, i.e., $CH_R+3$ would take on an illegal value of 152. Again, this is merely an example as other values for Q, N and P are contemplated.

In FIG. 11, other than the header row, each row in frequency-block hopping schedule 406 lists a frame number and the corresponding set CSET, i.e., FN(j) and CSET(j), where $CSET(j)=\{IF_R(BK(j,0))=IF_0, IF_1, IF_2, IF_3, IF_R(BK(j,1)=IF_4, IF_5, IF_6, IF_7\}$.

Again, there are two blocks of channels/IFs that comprise CSET(j), with the first block BK(j,0) being $IF_0$, $IF_1$, $IF_2$ and $IF_3$ where $IF_0$ is the root channel/IF, $IF_R(BK(j,0))$, and with the second block BK(j,1) being $IF_4$, $IF_5$, $IF_6$ and $IF_7$ where $IF_1$ is the root channel/IF, $IF_R(BK(j,1))$.

Recalling that frequency-block hopping schedule 406 can be derived from frequency-block hopping map 404 (again, as indicated by arrow 416 in FIG. 4), for frame FN(000), frequency-block hopping schedule 406 lists CSET(000)= $\{IF_R(BK(000,0))=IF_0=map(000)+0$, $IF_1=map(000)+1$, $IF_2=map(000)+2$, $IF_3=map(000)+3$, $IF_R(BK(000,1))=IF_4=map(255)+0$, $IF_5=map(255)+1$, $IF_6=map(255)+2$, $IF_7=map(255)+3\}$. Again, set CSET(000) represents the channels available to an instance of end node 102 for transmission thereover during frame FN(000), respectively.

In the next frame of schedule 412 of FIG. 11B, namely frame FN(001), CSET(001)=$\{IF_R(BK(001,0))=IF_0=map(000)+0$, $IF_1=map(000)+1$, $IF_2=map(000)+2$, $IF_3=map(000)+3$, $IF_R(BK(001,1))=IF_4=map(001)+0$, $IF_5=map(001)+1$, $IF_6=map(001)+2$, $IF_7=map(001)+3\}$. From frame FN(000) to frame FN(001), one block hops, namely hopping block $BK_H$=BK(001,1) corresponding to the channels/IFs: $IF_R(BK(001,1))=IF_4=map(001)+0$; $IF_5=map(001)+1$; $IF_6=map(001)+2$; and $IF_7=map(001)+3$.

In frame FN(002) of schedule 412 of FIG. 11B, CSET (002)=$\{IF_R(BK(002,0))=IF_0=map(002)+0$, $IF_1=map(002)+1$, $IF_2=map(002)+2$, $IF_3=map(002)+3$, $IF_R(BK(002,1))=IF_4=map(001)+0$, $IF_5=map(001)+1$, $IF_6=map(001)+2$, $IF_7=map(001)+3\}$. From frame FN(001) to frame FN(002), one block hops, namely hopping block $BK_H$=BK(002,0) corresponding to the channels/IFs: $IF_R(BK(002,0))=IF_0=map(002)+0$; $IF_1=map(002)+1$; $IF_2=map(002)+2$; and $IF_3=map(002)+3$.

In frame FN(003) of schedule 412 of FIG. 11B, CSET (003)=$\{IF_R(BK(003,0))=IF_0=map(002)+0$, $IF_1=map(002)+1$, $IF_2=map(002)+2$, $IF_3=map(002)+3$, $IF_R(BK(003,1))=IF_4=map(003)+0$, $IF_5=map(003)+1$, $IF_6=map(003)+2$, $IF_7=map(003)+3\}$. From frame FN(002) to frame FN(003), one block hops, namely hopping block $BK_H$=BK(003,1) corresponding to the channels/IFs: $IF_R(BK(003,1))=IF_4=map(003)+0$; $IF_5=map(003)+1$; $IF_6=map(003)+2$; and $IF_7=map(003)+3$.

In frame FN(004) of schedule 412 of FIG. 11B, CSET (004)=$\{IF_R(BK(004,0))=IF_0=map(004)+0$, $IF_1=map(004)+1$, $IF_2=map(004)+2$, $IF_3=map(004)+3$, $IF_R(BK(004,1))=IF_4=map(003)+0$, $IF_5=map(003)+1$, $IF_6=map(003)+2$, $IF_7=map(003)+3\}$. From frame FN(003) to frame FN(004), one block hops, namely hopping block $BK_H$=BK(004,0) corresponding to the channels/IFs: $IF_R(BK(004,0))=IF_0=map(004)+0$; $IF_1=map(004)+1$; $IF_2=map(004)+2$; and $IF_3=map(004)+3$.

Skipping ahead in schedule 412 of FIG. 11B, in frame FN(254), CSET(254)=$\{IF_R(BK(254,0))=IF_0=map(254)+0$, $IF_1=map(254)+1$, $IF_2=map(254)+2$, $IF_3=map(254)+3$, $IF_R(BK(254,1))=IF_4=map(253)+0$, $IF_5=map(253)+1$, $IF_6=map(253)+2$, $IF_7=map(253)+3\}$. From frame FN(253) to frame FN(2544), one block hops, namely hopping block $BK_H$=BK (2544,0) corresponding to the channels/IFs: $IF_R(BK(2544,0))=IF_0=map(2544)+0$; $IF_1=map(2544)+1$; $IF_2=map(254)+2$; and $IF_3=map(254)+3$.

In frame FN(255) of schedule 412 of FIG. 11B, CSET (255)=$\{IF_R(BK(255,0))=IF_0=map(254)+0$, $IF_1=map(254)+1$, $IF_2=map(254)+2$, $IF_3=map(254)+3$, $IF_R(BK(255,1))=IF_4=map(255)+0$, $IF_5=map(255)+1$, $IF_6=map(255)+2$, $IF_7=map(255)+3\}$. From frame FN(254) to frame FN(255), one block hops, namely hopping block $BK_H$=BK(255,1)

corresponding to the channels/IFs: $IF_R(BK(255,1))=$ $IF_4=map(255)+0$; $IF_5=map(255)+1$; $IF_6=map(255)+2$; and $IF_7=map(255)+3$}.

Frame FN(000) was discussed above. It is to be recalled that the hopping pattern prescribed by hopping schedule 406 in FIG. 11B is cyclical. Upon reaching frame FN(L-1)=FN (255), the next frame is understood to be FN(000). Accordingly, from frame FN(255) to frame FN(000), one block hops, namely hopping block $BK_H$=BK(000,0) corresponding to the channels/IFs: $IF_R(BK(000,0))=IF_0=map(000)+0$; $IF_1=map(000)+1$; $IF_2=map(000)+2$; and $IF_3=map(000)+3$.

Also in FIG. 11B, because N=2, it should be observed that each of blocks BK(j,0) and BK(j,1) stays the same for two frames and then changes on the third frame. Alternatively, for example, if N=3 (as in FIG. 9), then there would be blocks BK(j,0), BK(j,1) and BK(j,2), and each of those blocks would stay the same for three frames and then change on the fourth frame. In other words, the number of frames during which a block BK(j,e) (where $e \in \{0, 1, \ldots, N-1\}$ stays the same is dependent upon N.

Resuming discussion of the details of FIG. 11B, in the range of frames 000-005 and 246-255, BK(j,0) stays the same for frames 000-001, for frames 002-003, for frames 004-005, for frames 246-247, for frames 248-249, for frames 250-251, for frames 252-253 and for frames 254-255. In the range of frames 000-005 and 246-255, BK(j,1) stays the same for frames 001-002, for frames 003-004, for frames 005-006, for frames 247-248, for frames 249-250, for frames 251-252, for frames 253-254 and for frames 255-001.

Returning to FIG. 10, it is to be recalled that frequency-block hopping map 404 (a particular example of which is illustrated in FIG. 11A) can be derived from frequency-block hopping specification 402, as indicated by arrow 414. As noted, pseudo code is a particular implementation example of algorithm 408, with algorithm 408 being an implementation example of frequency-block hopping schedule 406 is algorithm 408, the latter being a species of frequency-block hopping guide. A yet more particular implementation example of algorithm 408 is the following example pseudo code.

Figure 12A:
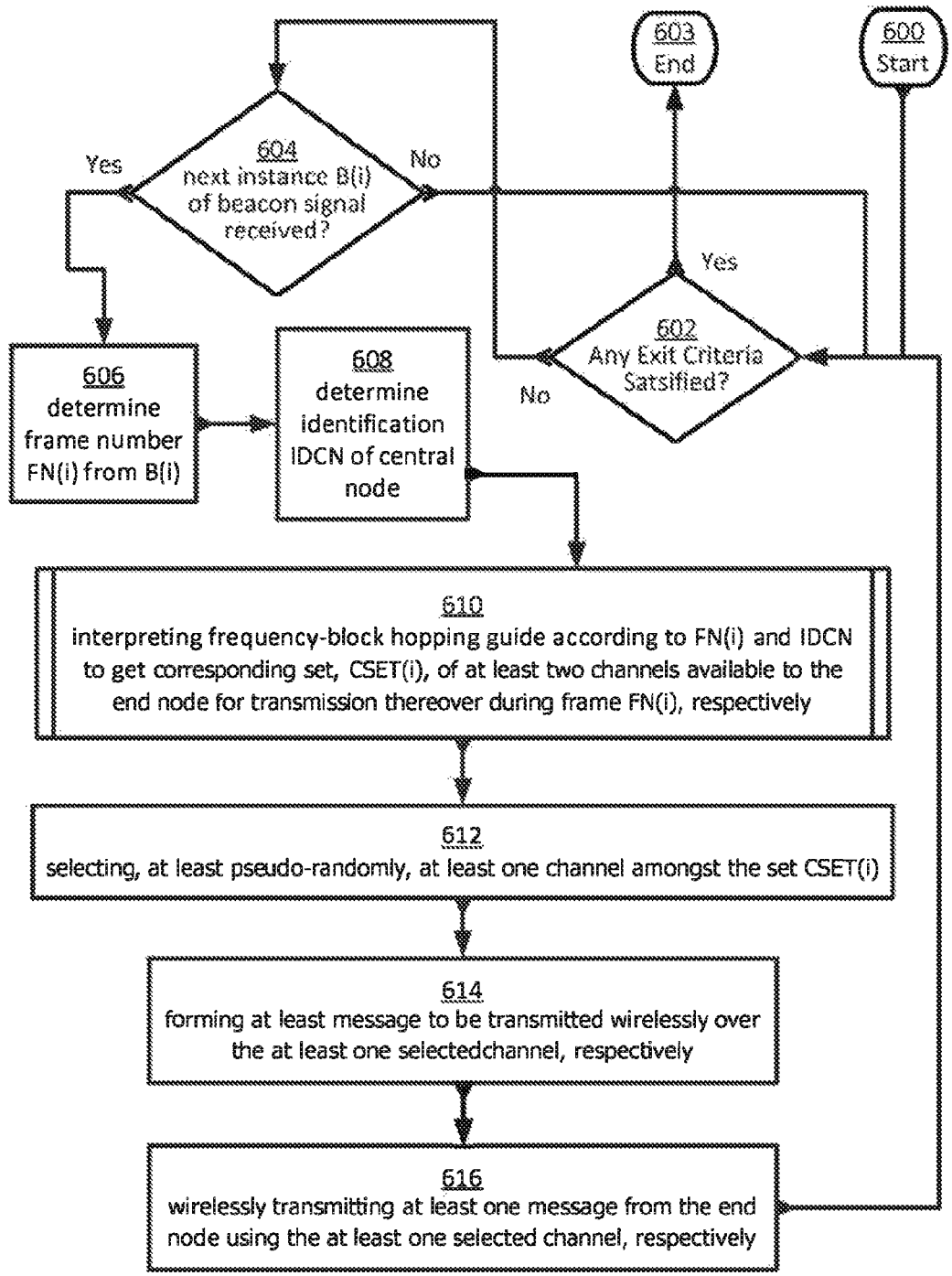
FIG. 12A is a flowchart illustrating a method of operating one instance of the end node, such as the collector, to wirelessly communicate with the central node over an unlicensed spectrum, according to an embodiment of the present invention.

Pseudo Code Example:
; >> assume L frames, where L is integer, 2≤L;
; >> assume Q uplink channels;
; >> assume N reception banks where N is integer, 2≤N;
; >> assume each bank has P contiguous channels;
; >> assume root channel, $CH_R$, amongst each instance of;
; P contiguous channels such that $CH_R(bnk(i),FN(j))$ denotes
; $CH_R$ for $i^{th}$ bank in $j^{th}$ frame, and such that, for a given block,
; there are P-1 other channels in addition to root channel $CH_R$; and
; such that, for the given block, the other P-1 channels can be
; determined based on the root channel $CH_R$;
Jump to pseudo code portion corresponding to value of IDCN;
Iterate over n, 0≤n≤L-1
  ; Determine which receiver bank to tune;
  BANK=n modulo N;
  Draw a pseudo random number s;
  Generate $CH_R$(BANK,FN(n)) based on s and each of $CH_R$(BANK,FN(n-1)), ..., $CH_R$(BANK,FN(n-(N-1)));
    Check if $CH_R$(BANK,FN(n)) is acceptable, i.e., if $CH_R$(BANK,FN(n)) does not violate any of the following rules:

$CH_R$(BANK,FN(n)) is different enough from each of $CH_R$(BANK,FN(n-1)), ..., $CH_R$(BANK, FN(n-(N-1))) to comply with hopping requirements for given unlicensed spectrum, and;
    $CH_R$(BANK,FN(n)) should be more than P channels away from $CH_R$(BANK,FN(n-1)), ..., $CH_R$(BANK,FN(n-(N-1)));
  If $CH_R$(BANK,FN(n)) is not acceptable, then loop to draw another pseudo random number;
  Else increment n and loop to next BANK;

FIG. 12A is a flowchart illustrating a method of operating one instance of end node 102 to wirelessly communicate with central node 106 over an unlicensed spectrum, according to an embodiment of the present invention.

In FIG. 12A, there is a loop. As a general design consideration, no loop should be infinite, i.e., inescapable. Accordingly, flow in FIG. 12A starts at block 600 and proceeds to a decision block 602, where processor 108 decides if any exit criteria have been satisfied. If the outcome of decision block 602 is yes (one or more of the exit criteria are satisfied), then flow proceeds to block 603 and ends. If the outcome of decision block 602 is no (none of the exit criteria has been satisfied), then flow proceeds to a decision block 604.

At decision block 604, processor 108 determines if a next instance B(i) of the beacon signal has been received via wireless unit 114'. An instance of end node 102 (via wireless unit 114' and wireless interface 114") can receive (downlink direction) an instance of the non-hopping beacon signal B periodically-transmitted from central node 106. Each instance B(i) of the beacon signal can include: a frame number FN(i) of a frame corresponding thereto; and identification IDCN of central node 106.

If the outcome of decision block 604 is no (the next instance B(i) of the beacon signal has NOT been received), then processor 108 waits, e.g., then flow loops back to the input of decision block 602. If the outcome of decision block 604 is yes (the next instance of the beacon signal HAS been received), then flow proceeds to a block 606.

At block 606, frequency-block hopping guide interpreter 138 can determine FN(i) from the payload of B(i). From block 606, flow proceeds to a block 608, where frequency-block hopping guide interpreter 138 can determine identification IDCN of central node 106. from the payload of B(i). Like central node 106, each instance of end node 102 includes an instance of frequency-block hopping guide interpreter 138. From block 608, flow proceeds to block 610, where frequency-block hopping guide interpreter 138 can interpret a frequency-block hopping guide according to FN(i) and IDCN thereby to determine a corresponding set, CSET(i), of at least two channels available to the instance of end node 102 for transmission thereover (uplink direction), respectively, during frame FN(i). From block 610, flow proceeds to a block 612.

At block 612, channel selector 142 can select, at least pseudo-randomly (albeit using a different pseudo random number generator than frequency-block hopping guide interpreter 138), at least one channel amongst the set CSET(i). From block 612, flow proceeds to a block 614, where message generator 144 generates at least one message to be transmitted over the at least one selected channel, respectively. From block 614, flow proceeds to a block 616, where wireless interface 114" (via wireless unit 114') wirelessly transmits (uplink direction) the at least one message resulting in at least one current transmission TRANS(e), respectively. From block 616, flow loops back to decision block 602, discussed above.

In general (and among other things), in terms of channel separation between a current transmission TRANS(e) and the preceding transmission TRANS(e−1) (which could be from the preceding frame FN(i−1) or an older frame FN(i−2), etc.), a larger gap (channel-gap) is better than a smaller channel-gap. For example, the at least one channel amongst the set CSET(i) can be chosen so that the channel-gap between the current transmission TRANS(e) and the preceding transmission TRANS(e−1) will be at least M contiguous channels, where M is a positive integer, N<M (again, N being the number of blocks in the set of channels CSET(j)), and P<M (again, P being the number of channels in each of the N blocks).

Figure 12B:
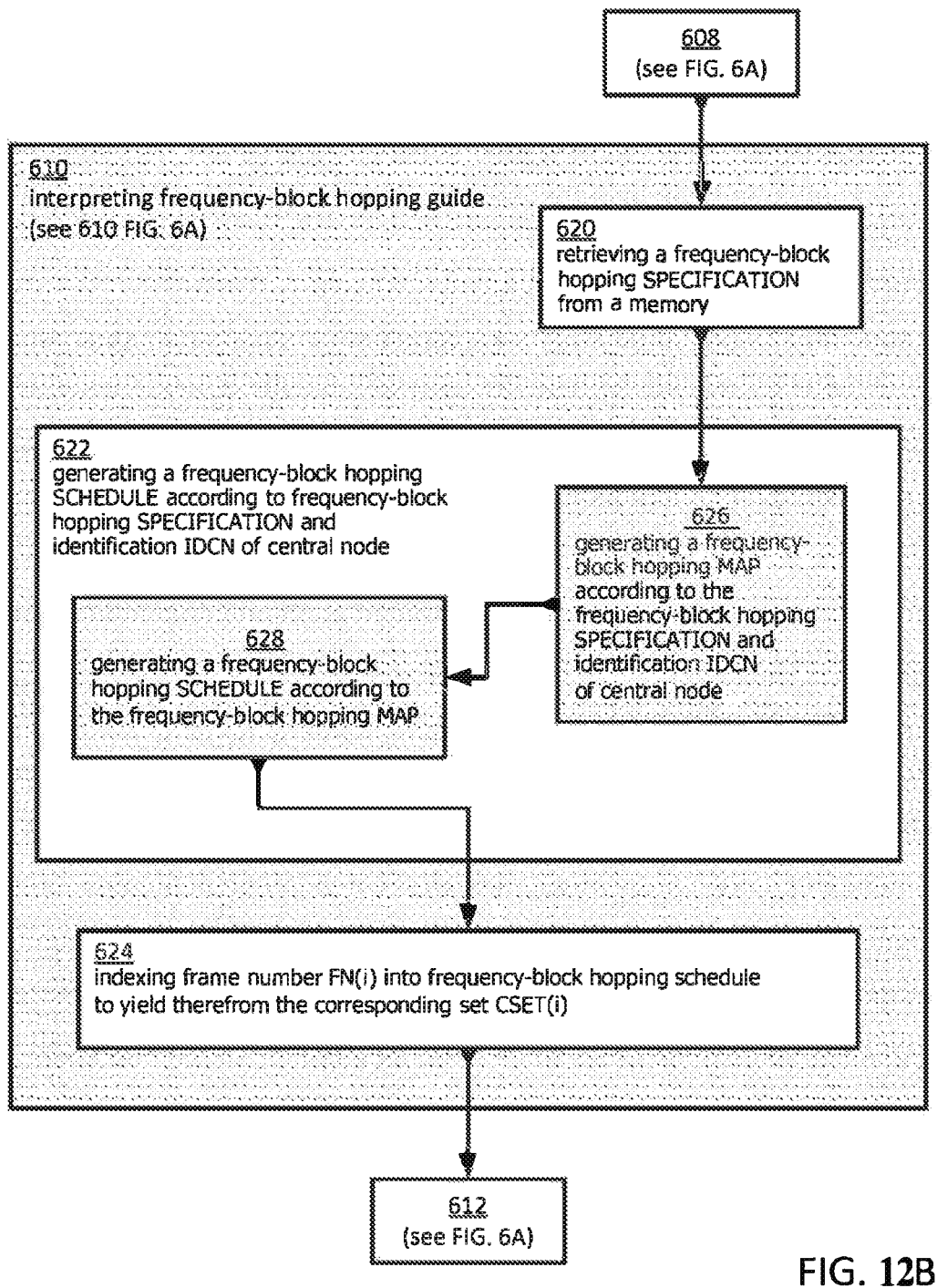
FIG. 12B is a flowchart illustrating a method of how an instance of the end node (i.e. collector) interprets a frequency-block hopping guide, according to an embodiment of the present invention.

FIG. 12B is a flowchart illustrating a method of how an instance of end node 102 interprets a frequency-block hopping guide, according to an embodiment of the present invention. More particularly, FIG. 12B provides details regarding flow inside block 610 of FIG. 12A.

In FIG. 12B, flow enters block 610 (from block 608 of FIG. 12A) and proceeds to a block 620, where processor 108 can retrieve a frequency-block hopping specification (e.g., block 402 of FIG. 10) from memory 110. From block 620, flow proceeds to a block 622, where processor 108 can generate a frequency-block hopping schedule (e.g., block 406 of FIG. 10) according to the frequency-block hopping specification and the identification IDCN of central node 106 (obtained at block 608 of FIG. 12A). Processor 108 can store the frequency-block hopping schedule in memory 110. From block 622, flow proceeds to a block 624.

At block 624, frequency-block hopping guide interpreter 138 can index the frame number FN(i) (obtained at block 606 of FIG. 12A) into the frequency-block hopping schedule to yield therefrom the corresponding set CSET(i). From block 624, flow leaves block 610 and proceeds to block 612 of FIG. 12A.

Upon proceeding from block 620 to block 622, flow can proceed within block 622 to a block 626, where processor 108 can generate a frequency-block hopping map (e.g., 404 of FIG. 10) based on the frequency-block hopping specification and the identification IDCN of central node 106. Processor 108 can store the frequency-block hopping map in memory 110. From block 626, flow can proceed to a block 628, where processor 108 can generate the frequency-block hopping schedule according to the frequency-block hopping specification. From block 628, flow leaves block 622 and proceeds to block 624, discussed above.

Figure 13A:
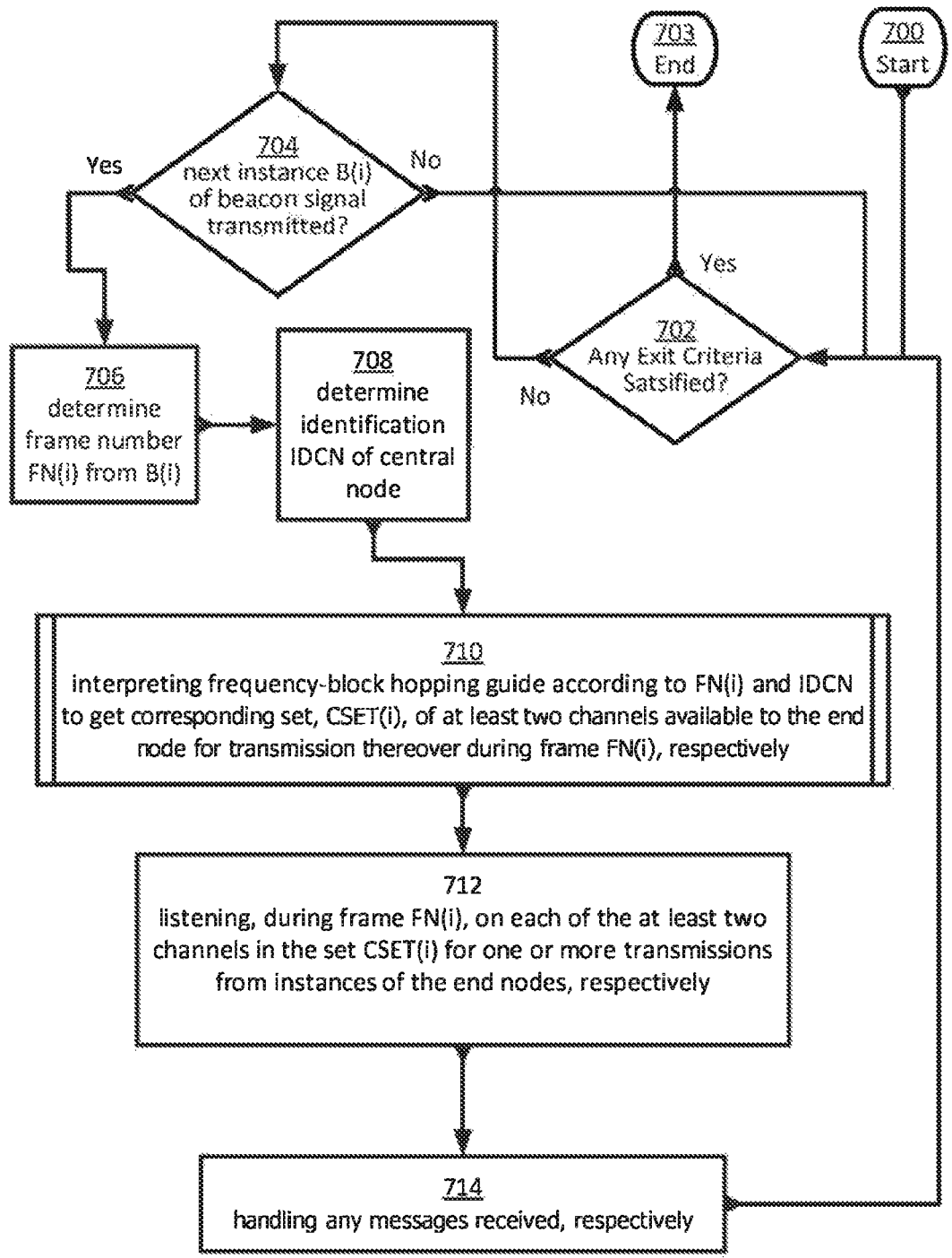
FIG. 13A is a flowchart illustrating a method of operating the central node to wirelessly communicate with instances of the end node (i.e. collector) over an unlicensed spectrum, according to an embodiment of the present invention.
Figure 13B:
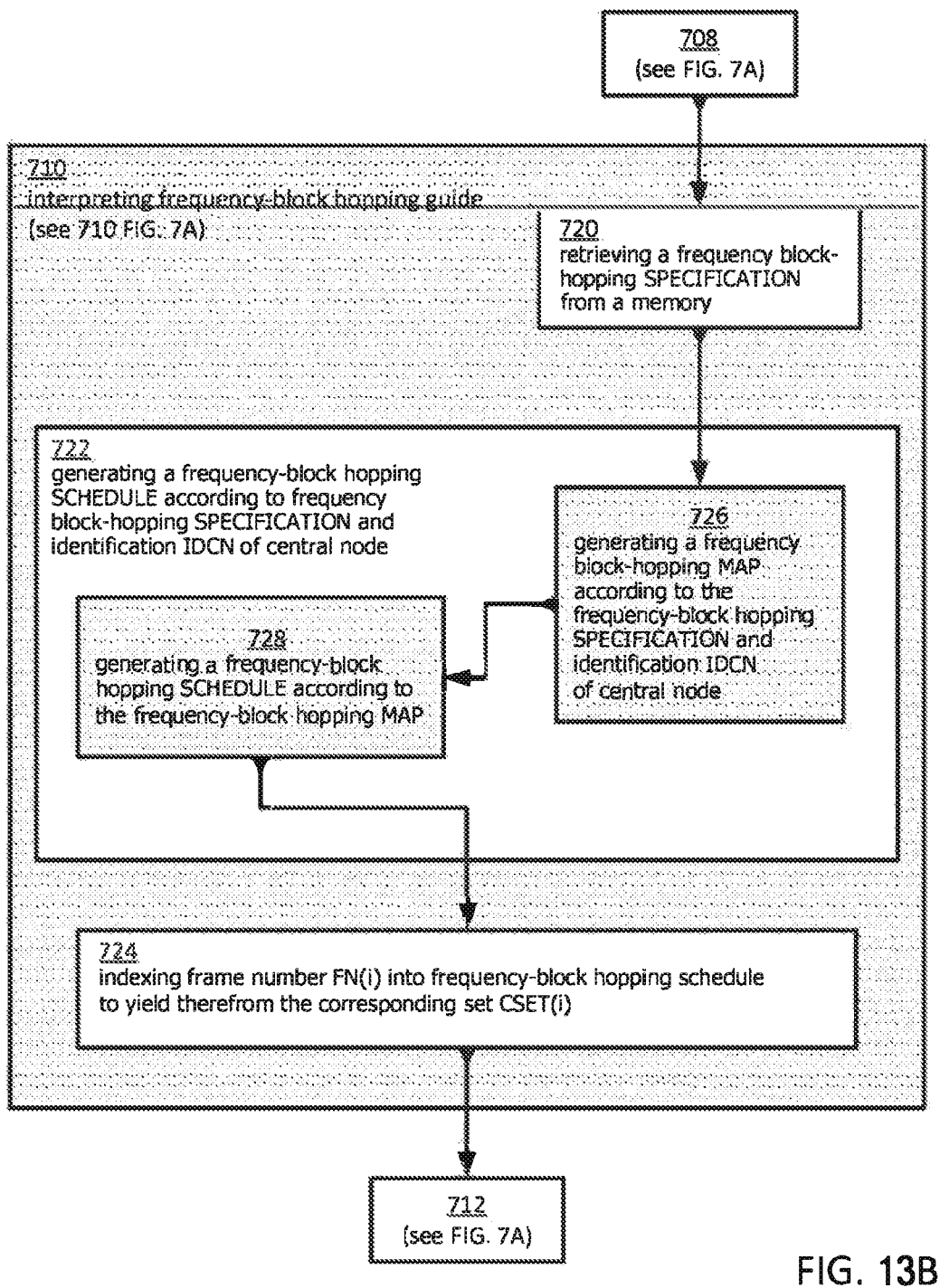
FIG. 13B is a flowchart illustrating a method of how the central node interprets a frequency-block hopping guide according to an embodiment of the present invention.

FIG. 13A is a flowchart illustrating a method of operating central node 106 to wirelessly communicate with instances of end node 102 (i.e. RTLS Collector in FIG. 1) over an unlicensed spectrum, according to an embodiment of the present invention. FIG. 13B is a flowchart illustrating a method of how the central node 106 (i.e. LPWAN Gateway in FIG. 1) interprets a frequency-block hopping guide according to an embodiment of the present invention.

In FIGS. 13A, 13B, there is a loop. As a general design consideration, no loop should be infinite, i.e., inescapable. Accordingly, flow in FIG. 13A starts at block 700 and proceeds to a decision block 702, where processor 116 decides if any exit criteria have been satisfied. If the outcome of decision block 702 is yes (one or more of the exit criteria are satisfied), then flow proceeds to block 703 and ends. If the outcome of decision block 702 is no (none of the exit criteria has been satisfied), then flow proceeds to a decision block 704.

At decision block 704, processor 116 determines if a next instance B(i) of the beacon signal has been transmitted via wireless unit 122'. Central node 106 can transmit periodically (via wireless unit 122' and wireless interface 122") an instance of the non-hopping beacon signal B. Each instance B(i) of the beacon signal can include: a frame number FN(i) of a frame corresponding thereto; and identification IDCN of central node 106. Again, frame tracker 136 can be configured to determine a frame number, FN(i). Beacon signal generator 134 can be configured to receive the frame number FN(i) and generate periodically an instance, B(i), of a non-hopping beacon signal B(i) which includes: the frame number, FN(i); and the identification, IDCN, of central node 106.

If the outcome of decision block 704 is no (the next instance B(i) of the beacon signal has NOT been transmitted), then processor 116 waits, e.g., then flow loops back to the input of decision block 702. If the outcome of decision block 704 is yes (the next instance of the beacon signal HAS been received), then flow proceeds to a block 706.

At block 706, frequency-block hopping guide interpreter 138 can determine FN(i) from the payload of B(i). From block 706, flow proceeds to a block 708, where frequency-block hopping guide interpreter 138 can determine identification IDCN of central node 106 from the payload of B(i). Like each instance of end node 102, central node 106 includes an instance of frequency-block hopping guide interpreter 138. From block 708, flow proceeds to block 710, where frequency-block hopping guide interpreter 138 can interpret a frequency-block hopping guide according to FN(i) and IDCN thereby to determine a corresponding set, CSET(i), of at least two channels available to the instances of end node 102 for transmission thereover (uplink direction), respectively, during frame FN(i). From block 710, flow proceeds to a block 712.

At block 712, 128 wireless interface 122", in particular N*P virtual receivers $128''_0, \ldots, 128''_{N-1}, 128''_N, \ldots, 128''_{N*P-1}$, listens (uplink direction) during frame FN(i), on each of the at least two channels in the set CSET(i) for one or more transmissions (uplink direction) from instances of end nodes 102, respectively. From block 712, flow proceeds to a block 714, where received-messages handler 140 can handle any of the received messages. From block 714, flow loops back to decision block 702, discussed above.

FIG. 13B is a flowchart illustrating a method of how central node 106 interprets a frequency-block hopping guide, according to an embodiment of the present invention. More particularly, FIG. 13B provides details regarding flow inside block 710 of FIG. 13A.

In FIG. 13B, flow enters block 710 (from block 708 of FIG. 13A) and proceeds to a block 720, where processor 116 can retrieve a frequency-block hopping specification (e.g., block 402 of FIG. 10) from memory 118. From block 720, flow proceeds to a block 722, where processor 116 can generate a frequency-block hopping schedule (e.g., block 406 of FIG. 10) according to the frequency-block hopping specification and the identification IDCN of central node 106 (obtained at block 708 of FIG. 13A). Processor 116 can store the frequency-block hopping schedule in memory 118. From block 722, flow proceeds to a block 724.

At block 724, frequency-block hopping guide interpreter 138 can index the frame number FN(i) (obtained at block 706 of FIG. 13A) into the frequency-block hopping schedule to yield therefrom the corresponding set CSET(i). From block 724, flow leaves block 710 and proceeds to block 712 of FIG. 13A.

Upon proceeding from block 720 to block 722, flow can proceed within block 722 to a block 726, where processor 116 can generate a frequency-block hopping map (e.g., 404 of FIG. 10) based on the frequency-block hopping specification and the identification IDCN of central node 106. Processor 116 can store the frequency-block hopping map in memory 118. From block 726, flow can proceed to a block 728, where processor 116 can generate the frequency-block hopping schedule according to the frequency-block hopping specification. From block 728, flow leaves block 722 and proceeds to block 724, discussed above.

In the embodiments discussed above, for simplicity, it has been assumed that the P channels in each of the N blocks are contiguous. Alternatively, other groupings of the P channels in each of the N blocks are contemplated. For example, the P channels in each of the N blocks could be even sequential channels, odd sequential channels, etc.

Advantages of at least some, if not all, of the embodiments disclosed herein include: greater design flexibility because it is not necessary to provide Q receivers for Q uplink channels, rather N receivers are provided, where N<Q; a reduced amount of receiver re-tuning because only one bank of receivers (one block of frequencies included within the set of N frequency-blocks that comprise set CSET) re-tunes from one frame FN(j) to the next FN(j+1), which thereby reduces system downtime, increases capacity and relaxes the time synchronization constraints; interference mitigation, e.g., even active interference avoidance (cognitive radio); etc.

The present invention is not limited to the particular embodiments illustrated in the drawings and described above in detail. Those skilled in the art will recognize that other arrangements could be devised. The present invention encompasses every possible combination of the various features of each embodiment disclosed. One or more of the elements described herein with respect to various embodiments can be implemented in a more separated or integrated manner than explicitly described, or even removed or rendered as inoperable in certain cases, as is useful in accordance with a particular application While the present invention has been described with reference to specific illustrative embodiments, modifications and variations of the present invention may be constructed without departing from the spirit and scope of the present invention as set forth in the following claims.

While the present invention has been described in the context of the embodiments explicitly discussed herein, those skilled in the art will appreciate that the present invention is capable of being implemented and distributed in the form of a computer-usable medium (in a variety of forms) containing computer-executable instructions, and that the present invention applies equally regardless of the particular type of computer-usable medium which is used to carry out the distribution. An exemplary computer-usable medium is coupled to a computer such the computer can read information including the computer-executable instructions therefrom, and (optionally) write information thereto. Alternatively, the computer-usable medium may be integral to the computer. When the computer-executable instructions are loaded into and executed by the computer, the computer becomes an apparatus for practicing the invention. For example, when the computer-executable instructions are loaded into and executed by a general-purpose computer, the general-purpose computer becomes configured thereby into a special-purpose computer. Examples of suitable computer-usable media include: volatile memory such as random access memory (RAM); nonvolatile, hard-coded or programmable-type media such as read only memories (ROMs) or erasable, electrically programmable read only memories (EEPROMs); recordable-type and/or re-recordable media such as floppy disks, hard disk drives, compact discs (CDs), digital versatile discs (DVDs), etc.; and transmission-type media, e.g., digital and/or analog communications links such as those based on electrical-current conductors, light conductors and/or electromagnetic radiation.

Although the present invention has been described in detail, those skilled in the art will understand that various changes, substitutions, variations, enhancements, nuances, gradations, lesser forms, alterations, revisions, improvements and knock-offs of the invention disclosed herein may be made without departing from the spirit and scope of the invention in its broadest form.

What is claimed is:

1. A method of identifying a location of one or more objects to be located in real time, comprising:
   sending a beacon advertisement message from an object, to be located from among the objects to be located in real time, to a collector via a first wireless communications protocol, the first wireless communications protocol being a short range radio frequency communications protocol, the beacon advertisement message including a unique MAC (Media Access Control) address;
   processing the beacon advertisement message at the collector, thereby creating a collector processing result;
   sending the collector processing result from the collector to a gateway via a second wireless communications protocol, the second wireless communications protocol being a low power wide area network communications protocol;
   relaying the collector processing result from the gateway to one or more upstream components;
   further processing the collector processing result, thereby determining the unique MAC address corresponds to the object and creating a location identification processing result, the location identification processing result identifying the location of the object; and
   displaying the location identification processing result on an end user terminal,
   wherein the gateway is configured to communicate with the one or more upstream components so as to establish selective identification and location determination, by one or more of the upstream components and from among the objects to be located in real time, of the object to be located and which sends the beacon advertisement message that is processed to create the collector processing result.

2. The method of claim 1, wherein the second wireless communications protocol is a chirp spread spectrum radio modulation format that transmits the collector processing result over a long range between the collector and the gateway.

3. The method of claim 2, wherein the second communications protocol includes receiving wirelessly a current instance of a beacon signal periodically-transmitted;
   measuring a received power, PB-RX, of the beacon signal;
   reading locally-stored values of PB-TX and G representing a presumed transmitted power of the beacon signal and a performance goal, respectively;
   determining, for a given channel, a path loss, PL, based on the PB-RX and the PB-TX; and
   adaptively setting an energy level, EN-TX, of a forthcoming signal to be transmitted based on PL and G.

4. The method of claim 3, wherein the adaptively setting includes:
   adaptively determining, for the forthcoming signal, at least two of:

a level of power, PN-TX;
a forward error correction coding rate, c; and
a spreading factor, SF; and
a modulation format, M.

5. The method of claim 4, wherein the adaptively determining includes:
solving a standard optimization problem using the PL and the G as inputs to find a desirable minimized combination of the least two of:
a level of power, PN-TX;
a forward error correction coding rate, c; and
a spreading factor, SF; and
a modulation format, M.

6. The method of claim 3, wherein values of the performance goal G include:
values that maximize data-reliability of the data as received at the central node;
values that optimize the energy level EN-TX relative to battery-chemistry-specific attributes of the battery sourcing the end node; and
values that reflect a desired ratio of data-reliability versus battery management.

7. The method of claim 3, wherein:
the transmitted power, PB-TX, of the beacon signal changes over time; and
the method further comprises:
receiving instances of a configuration signal periodically-transmitted from the central node, each instance including a value representing a transmitted power, PB-TX, of forthcoming instances of the beacon signal; and
storing the received value of PB-TX locally as the presumed transmitted power of the beacon signal.

8. The method of claim 7, wherein:
the configuration signal is received at an interval, ICONFIG; and
the beacon signal is received at an interval, IBEACON; and
at least one of the following relations is true:
IBEACON<ICONFIG;
ICONFIG=15*(IBEACON); and
ICONFIG=30 seconds and IBEACON=2 seconds.

9. The method of claim 3, wherein the second wireless communications protocol includes wirelessly transmitting according to the energy level EN-TX.

10. The method of claim 9, wherein the second wireless communications protocol includes wirelessly transmitting in an unlicensed spectrum, and the beacon signal is a non-hopping signal.

11. The method of claim 2, wherein the second wireless communications protocol includes communicating over an unlicensed spectrum, further including:
wirelessly receiving, an instance of a non-hopping beacon signal, B, periodically-transmitted;
each instance B(i) of the beacon signal including:
a frame number, FN(i), of a frame corresponding thereto; and
an identification, IDCN, of the gateway;
interpreting a frequency-block hopping guide according to FN(i) and IDCN thereby to determine a corresponding set, CSET(i), of at least two channels available to the end node for transmission thereover, respectively, during frame FN(i);
wherein the frequency-block hopping guide establishes:
a total of L frames;
a set of channels CSET for each frame, respectively; and
that, for any two consecutive ones of the L frames, FN(j) and FN(j+1), the corresponding sets CSET(j) and CSET(j+1) will be different, CSET(j)≠CSET(j+1);
selecting, at least pseudo-randomly, at least one channel amongst the set CSET(i); and
wirelessly transmitting at least one message using the at least one selected channel, respectively;
wherein i and j are non-negative integers, L is an integer and 2≤L.

12. The method of claim 11, wherein the frequency-block hopping guide, for any given frame FN(j), further establishes:
the corresponding set of channels CSCET(j) includes N blocks, 2≤N;
each block in CSET(i) includes P contiguous channels, 2≤P;
each channel in CSET(j) is a member of only one of the blocks of CSET(j); and
N and P are positive integers.

13. The method of claim 12, wherein the frequency-block hopping guide further establishes:
how, for any two consecutive ones of the L frames, FN(j) and FN(j+1), channels comprising only one of the N blocks, block BKH, change between the corresponding sets CSET(j) and CSET(j+1) such that BKH(j)≠BKH(j+1), thereby establishing how the block BKH hops between CSET(j) and CSET(j+1).

14. The method of claim 11, wherein the interpreting a frequency-block hopping guide includes:
retrieving a frequency-block hopping specification from a memory;
generating a frequency-block hopping schedule according to the frequency-block hopping specification and the identification IDCN of the gateway; and
indexing the frame number FN(i) into the frequency-block hopping schedule to yield therefrom the corresponding set CSET(i).

15. The method of claim 14, wherein:
generating a frequency-block hopping map based on the frequency-block hopping specification and the identification IDCN of the gateway; and
generating the frequency-block hopping schedule based on the frequency-block hopping map.

16. The method of claim 14, wherein the generating the frequency-block hopping schedule includes:
organizing the L instances of sets CSET of channels into a data structure that identifies, for each of the L instances of frame number FN, the N*P channels in the corresponding instance of set CSET, respectively, with the data structure being the frequency-block hopping schedule.

17. A system for identifying the location of one or more objects to be located in real time, the system comprising:
an object to be located, from among the objects to be located in real time, including a short range radio frequency signal transmitter for transmitting a signal with unique information that is associated with, and thereby identifies, the object using a first wireless communications protocol;
a collector within a short range radio frequency signal range of the object, the collector including a signal receiver for receiving the signal with unique information that is associated with, and thereby identifies, the object using the first wireless communications protocol, the collector further including a transmitter for transmitting the signal including the unique information that is associated with the object using a second wireless communication protocol via a low power wide area network;

a gateway in wireless communication with the collector via the low power wide area network, the gateway including a receiver for receiving the signal with information including the unique information that is associated with the object from the collector;

a processing application for processing the information, including determining the association between the unique information and the object thereby identified, and creating an information processing outcome; and an end user terminal having an interface for displaying the information processing outcome, wherein the gateway is configured to communicate with one or more of the processing application and the end user terminal so as to establish selective identification and location determination, by one or more of the processing application and the end user terminal and from among the objects to be located in real time, of the object transmitting the signal with the unique information.

18. The system of claim 17, wherein the object is a hospital bed located in a hospital.

19. The system of claim 17, wherein the object is a human laborer located in an agricultural field.

20. The system of claim 17, wherein the object is a human laborer located at a construction site.

21. The system of claim 17, wherein the collector is battery powered.

22. A system for transmitting information using two different wireless communication protocols, the system comprising:

an object to be located, from among a plurality of objects, including a short range radio frequency signal transmitter for transmitting a signal using a first wireless communications protocol, the signal including information transmitted from the object;

a collector within a short range radio frequency signal range of the object, the collector including a signal receiver for receiving the signal transmitted by the short range radio frequency transmitter using the first wireless communications protocol, the collector further including a collector transmitter that transmits a collector signal using a second wireless communication protocol via a low power wide area network, the collector signal including the information transmitted from the object;

a gateway in wireless communication with the collector via the low power wide area network, the gateway including a gateway receiver for receiving the collector signal;

a processing application for processing the information transmitted from the object and creating an information processing outcome; and an end user terminal having an interface for displaying the information processing outcome, wherein the gateway is configured to communicate with one or more of the processing application and the end user terminal so as to establish selective identification and location determination, by one or more of the processing application and the end user terminal and from among the plurality of objects, of the object transmitting the signal including the information transmitted from the object.

23. The system of claim 22, wherein the object is a temperature sensor and the information transmitted from the object is a sensed temperature.

24. The system of claim 22, wherein the object is utility meter and the information transmitted from the object includes a utility usage volume.

25. The system of claim 24, wherein the utility is selected from the list comprising: water, gas and electricity.

26. The system of claim 22, wherein the object is a sensor that senses the presence of a condition and the information transmitted from the object includes a state with respect to the presence of the condition.

27. The system of claim 26, wherein the condition is selected from a list comprising: a door being opened, a door being locked, and a toxic gas being present in a predetermined concentration level.

28. The system of claim 22, wherein the object is a consumable dispenser and the information transmitted from the object is selected from a list consisting of: an amount of a consumable dispensed by the dispenser, a time during which dispensing of the consumable occurred, and a time when the dispenser is opened and the consumable is changed or replaced.

29. The system of claim 28, wherein the consumable is selected from the list comprising: paper towels and liquid soap.

* * * * *